(12) United States Patent
Kikuchi

(10) Patent No.: US 8,243,268 B2
(45) Date of Patent: Aug. 14, 2012

(54) SUBSTRATE PROCESSING APPARATUS, OPTICAL CONSTANT OBTAINING METHOD, AND STORAGE MEDIUM STORING PROGRAM EXECUTING SAME

(75) Inventor: Toshihiko Kikuchi, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 315 days.

(21) Appl. No.: 12/543,697

(22) Filed: Aug. 19, 2009

(65) Prior Publication Data

US 2010/0045981 A1     Feb. 25, 2010

(30) Foreign Application Priority Data

Aug. 21, 2008   (JP) .................................. 2008-213074

(51) Int. Cl.
*G01J 3/00* (2006.01)

(52) U.S. Cl. ........ 356/300; 356/401; 356/121; 428/432; 428/426; 428/446; 428/448

(58) Field of Classification Search .................. 356/503, 356/504, 401, 121, 300; 428/432, 426, 446, 428/448

See application file for complete search history.

(56) References Cited

U.S. PATENT DOCUMENTS

| | | | | |
|---|---|---|---|---|
| 5,883,720 A * | 3/1999 | Akiyama et al. | ............... | 356/632 |
| 6,392,756 B1 * | 5/2002 | Li et al. | ........................ | 356/632 |
| 6,645,045 B2 * | 11/2003 | Ohkawa | ........................... | 451/6 |
| 6,825,938 B2 * | 11/2004 | Mikami et al. | ................ | 356/630 |
| 7,012,699 B2 * | 3/2006 | Shinya et al. | ................. | 356/504 |
| 7,145,662 B2 * | 12/2006 | Jeong et al. | ................... | 356/504 |
| 7,414,713 B2 * | 8/2008 | Yamamoto | .................... | 356/123 |
| 7,586,622 B1 * | 9/2009 | Ramakrishnan et al. | ..... | 356/504 |
| 7,663,760 B2 * | 2/2010 | Kikuchi | ........................ | 356/445 |

FOREIGN PATENT DOCUMENTS

JP   2002-260994   9/2002
JP   2005-33187    2/2005

* cited by examiner

*Primary Examiner* — Gregory J Toatley
*Assistant Examiner* — Isiaka Akanbi
(74) *Attorney, Agent, or Firm* — Oblon, Spivak, McClelland, Maier & Neustadt, L.L.P.

(57) ABSTRACT

In a method of obtaining an optical constant of each the films of a film-stacked structure formed on a substrate, a basic process obtains an optical constant of each of the films by successively providing the films one by one as a target film from bottom to top and obtaining an optical constant of the target film by using a previously obtained optical constant of a below-located film that is located below the target film and a re-obtaining process re-obtains the optical constant of each of the films by correcting the previously obtained optical constant of the below-located film and the optical constant of the target film obtained in the basic process.

13 Claims, 14 Drawing Sheets

FIG. 6

| FILM STRUCTURE SAMPLE | ACTUAL-MEASURED SPECTRUM | FITTING | | OPTICAL CONSTANT |
|---|---|---|---|---|
| | | OPTICAL CONSTANT PARAMETER | FILM THICKNESS | |
| A <br> $d_{A1}$ : $n_1, k_1 \rightarrow P_1$ — 530a, 520a, 510a | $I_A$ | $P_1$ | $d_{A1}$ | $n_1, k_1$ |
| B <br> $d_{B2}$ : $n_2, k_2 \rightarrow P_2$ — 540b <br> $d_{B1}$ : $n_1, k_1 \rightarrow P_1$ — 530b, 520b, 510b | $I_B$ | $P_2$ | $d_{B1}, C_{B2}$ | $n_2, k_2$ |
| C <br> $d_{C3}$ : $n_3, k_3 \rightarrow P_3$ — 550c <br> $d_{C2}$ : $n_2, k_2 \rightarrow P_2$ — 540c <br> $d_{C1}$ : $n_1, k_1 \rightarrow P_1$ — 530c, 520c, 510c | $I_C$ | $P_3$ | $d_{C1}, C_{D2}, d_{C3}$ | $n_3, k_3$ |
| D <br> $d_{D4}$ : $n_4, k_4 \rightarrow P_4$ — 560d <br> $d_{D3}$ : $n_3, k_3 \rightarrow P_3$ — 550d <br> $d_{D2}$ : $n_2, k_2 \rightarrow P_2$ — 540d <br> $d_{D1}$ : $n_1, k_1 \rightarrow P_1$ — 530d, 520d, 510d | $I_D$ | $P_4$ | $d_{D1}, d_{D2}, d_{D3}, d_{D4}$ | $n_4, k_4$ |

FIG.16

| | | FITTING SPECTRUM (FITTING PARAMETER) | OBTAINED OPTICAL CONSTANTS |
|---|---|---|---|
| FIRST PROCESS | FIRST OPERATION | $I_A, S_A(P_1, d_{A1})$ | $n1a1, k1a1$ |
| SECOND PROCESS | FIRST OPERATION | $I_B, S_B(P_2, d_{B1}, d_{B2})$ | $n2b1, k2b1$ |
| | SECOND OPERATION | ① $I_B, S_B(P_1, P_2, d_{B1}, d_{B2})$<br>② $I_A, S_A(P_1, d_{A1})$ | $n2b2, k2b2$<br>$n1b2, k1b2$ |
| THIRD PROCESS | FIRST OPERATION | $I_C, S_C(P_3, d_{C1}, d_{C2}, d_{C3})$ | $n3c1, k3c1$ |
| | SECOND OPERATION | ① $I_C, S_C(P_2, P_3, d_{C1}, d_{C2}, d_{C3})$<br>② $I_B, S_B(P_2, d_{B1}, d_{B2})$ | $n3c2, k3c2$<br>$n2c2, k2c2$ |
| | THIRD OPERATION | ① $I_C, S_C(P_1, P_2, P_3, d_{C1}, d_{C2}, d_{C3})$<br>② $I_B, S_B(P_1, P_2, d_{B1}, d_{B2})$<br>③ $I_A, S_A(P_1, d_{A1})$ | $n3c3, k3c3$<br>$n2c3, k2c3$<br>$n1c3, k1c3$ |
| FOURTH PROCESS | FIRST OPERATION | $I_D, S_D(P_4, d_{D1}, d_{D2}, d_{D3}, d_{D4})$ | $n4d1, k4d1$ |
| | SECOND OPERATION | ① $I_D, S_D(P_3, P_4, d_{D1}, d_{D2}, d_{D3}, d_{D4})$<br>② $I_C, S_C(P_3, d_{C1}, d_{C2}, d_{C3})$ | $n4d2, k4d2$<br>$n3d2, k3d2$ |
| | THIRD OPERATION | ① $I_D, S_D(P_2, P_3, P_4, d_{D1}, d_{D2}, d_{D3}, d_{D4})$<br>② $I_C, S_C(P_2, P_3, d_{C1}, d_{C2}, d_{C3})$<br>③ $I_B, S_B(P_2, d_{B1}, d_{B2})$ | $n4d3, k4d3$<br>$n3d3, k3d3$<br>$n2d3, k2d3$ |
| | FOURTH OPERATION | ① $I_D, S_D(P_1, P_2, P_3, P_4, d_{D1}, d_{D2}, d_{D3}, d_{D4})$<br>② $I_C, S_C(P_1, P_2, P_3, d_{C1}, d_{C2}, d_{C3})$<br>③ $I_B, S_B(P_1, P_2, d_{B1}, d_{B2})$<br>④ $I_A, S_A(P_1, d_{A1})$ | $n4d4, k4d4$<br>$n3d4, k3d4$<br>$n2d4, k2d4$<br>$n1d4, k1d4$ |

SUBSTRATE PROCESSING APPARATUS, OPTICAL CONSTANT OBTAINING METHOD, AND STORAGE MEDIUM STORING PROGRAM EXECUTING SAME

CROSS-REFERENCE TO RELATED APPLICATIONS

This application claims priority to Japanese Patent Application No. 2008-213074, filed on Aug. 21, 2008, the entire contents of which are hereby incorporated by reference.

FIELD OF THE INVENTION

The present invention relates to a substrate processing apparatus, an optical constant obtaining method, and a storage medium storing a program that executes the optical constant obtaining method.

BACKGROUND OF THE INVENTION

With recent requirement for ever decreasing sizes of semiconductor devices, it has become necessary to more finely form a circuit pattern on a surface of a semiconductor wafer. In order to form such a fine circuit pattern, in the manufacturing process of semiconductor devices, it is required to accurately examine a surface structure of a wafer in which a plurality of films is stacked, e.g., a wafer of each film after an etching process is performed.

Conventionally, after the wafer is etched, a surface structure of the wafer is examined by observing and photographing the cross section of the cleaved wafer with a scanning electron microscope (SEM). To employ such a method, it is inevitable to cut the wafer to observe the cross section of the wafer.

Accordingly, to examine the surface structure of the wafer without destructing the wafer after the etching process is performed, there has recently been developed a method of applying scatterometry such as elipsometry or reflectometry, which has been used for evaluation of a resist pattern or the like, to examination of the surface structure of a wafer (see, e.g., Japanese Patent Laid-open Application No. 2002-260994).

Especially, by employing the reflectometry as the scatterometry, it is possible to examine the surface structure of the wafer without destructing the wafer by using optical constants (a refractive index n and an attenuation constant k) of the surface structure of the wafer. In detail, the optical constants n and k of each film stacked on the surface of a wafer, e.g., a gate oxide film, a polysilicon film, an oxide film, a bottom anti-reflective coating (BARC) film, and a photoresist film, are estimated. Next, optical models representing surface structures, e.g., groove patterns of the wafer are developed and stored for various groove patterns by using the estimated optical constants of the respective films. Then, the surface structure (e.g., a groove pattern) of the wafer is examined by measuring a surface reflectance of the wafer and selecting a model of the groove pattern corresponding to the reflectance (see, e.g., Japanese Patent Laid-open Application No. 2005-033187).

Accordingly, in the scatterometry, when the optical constants of the respective films are not accurately obtained, it may be difficult to accurately examine the surface structure of the wafer. As a result, it becomes very important to accurately obtain the optical constants of the respective films.

A so-called fitting method is conventionally employed to obtain the optical constants. In the fitting, a white beam is emitted to an object film, and a reflected beam of the white beam is measured to obtain an actually measured spectrum of a spectral reflectance. Then, in the fitting, the optical constants are obtained by employing a theoretical model to fit the actually measured spectrum, wherein a set of fitting parameters of the model which is used to produce the optical constants is determined such that the set gives the theoretical model a best fit to the measured actually measured spectrum. At the time when the fitting is performed, it is possible to reduce the number of parameters by fixing optical constants of a below-located film that is located below a target film with values obtained previously, thereby decreasing the obtaining time.

However, if previously obtained optical constants of a below-located film that is located below a target film are used in the obtaining process of the optical constants of the respective films, even though the optical constants of the below-located film have been obtained through the satisfactory fitting, optical constants of the target film located above the below-located film may be obtained through an unsatisfactory fitting. This may deteriorate the accuracy in the optical constants of the film.

In the fitting, the optical constants are fundamentally obtained by acquiring a combination of parameters that minimizes the difference between the actually measured spectrum and the theoretical spectrum. Accordingly, since the optical constants are obtained when the theoretical spectrum fits best to the actually measured spectrum, it is considered that the optical constants are adequate.

However, since a plurality of unknown parameters is changed in the fitting, the more the number of the unknown parameters, the more their combinations there are. Accordingly, there may be a plurality of local minimum solutions (i.e., combinations of the parameters) to minimize the difference between the actually measured spectrum and the theoretical spectrum. In this case, even though certain local minimum solutions, i.e., certain combinations of the parameters are mathematically correct, all the certain combinations may not be physically correct. If the optical constants of the below-located film are not physically correct, when the optical constants of the target film located above the below-located film are obtained by using the physically incorrect optical constants, it is highly likely that the fitting is unsatisfactorily performed.

SUMMARY OF THE INVENTION

In view of the above, the present invention provides an optical constant obtaining method capable of improving a calculating accuracy in optical constants of each film of a film-stacked structure on a substrate.

In accordance with an aspect of the present invention, there is provided a method of obtaining an optical constant of each of the films of a film-stacked structure formed on a substrate, including: a basic process obtaining an optical constant of each of the films by successively providing the films one by one as a target film from bottom to top and obtaining an optical constant of the target film by using a previously obtained optical constant of a below-located film that is located below the target film; and a re-obtaining process for re-obtaining the optical constant of each of the films by correcting the previously obtained optical constant of the below-located film and the optical constant of the target film obtained in the basic process.

In accordance with another aspect of the present invention, there is provided a substrate processing apparatus of obtaining an optical constant of each film of a film-stacked structure formed on a substrate, including: a measuring chamber configured to include at least a light source to emit a white beam over the substrate, a spectrometer to disperse a reflection beam of the white beam into its spectrum, and a detector to detect a beam from the spectrometer; and a control device, configured to control the measuring chamber. The control device acquires an actually measured spectrum of a spectral reflectance by emitting a white beam to a substrate formed with a film structure sample required for obtaining an optical constant of each film of the film-stacked structure and detecting a reflection beam of the white beam and performs a basic process obtaining the optical constant of each of the films successively from bottom to top by a fitting to the actually measured spectrum and a theoretical spectrum and a re-obtaining process for re-obtaining the optical constant of each of the films by correcting the previously obtained optical constant of the below-located film and the optical constant of the target film obtained in the basic process.

In accordance with yet another aspect of the present invention, there is provided a computer-readable storage medium storing a computer-readable program for executing a method of obtaining an optical constant of each film of a film-stacked structure formed on a substrate, including: a basic process obtaining an optical constant of each of the films by successively providing the films one by one as a target film from bottom to top and obtaining an optical constant of the target film by using a previously obtained optical constant of a below-located film that is located below the target film; and a re-obtaining process for re-obtaining the optical constant of each of the films by correcting the previously obtained optical constant of the below-located film and the optical constant of the target film obtained in the basic process.

In accordance with an embodiment of the present invention, when any film(s) of the films for obtaining their optical constants is provided as a target sample film(s), the optical constants of the target sample film(s) are obtained in the basic process and the optical constants of the target sample film(s) are re-obtained by correcting the optical constants of the target sample film(s) and the optical constants of below-located sample film(s) that is located below the target sample film(s) in the re-obtaining process. Accordingly, the optical constants of the below-located sample films can be corrected to physically correct values, thereby improving the accuracy in obtaining the optical constants of the target sample film(s) as well as the below-located sample films. Further, it is possible to improve the accuracy in obtaining the optical constants of each sample film.

BRIEF DESCRIPTION OF THE DRAWINGS

The objects and features of the present invention will become apparent from the following description of embodiments, given in conjunction with the accompanying drawings, in which:

FIG. 6 is a table showing film structure samples required for obtaining optical constants of each film shown in FIG. 5;

FIG. 16 is a table showing a flow of a recalculation step performed after a basic process which are performed to obtain the optical constants of each film of the film-stacked structure shown in FIG. 5;

DETAILED DESCRIPTION OF THE EMBODIMENT

Figure 1:
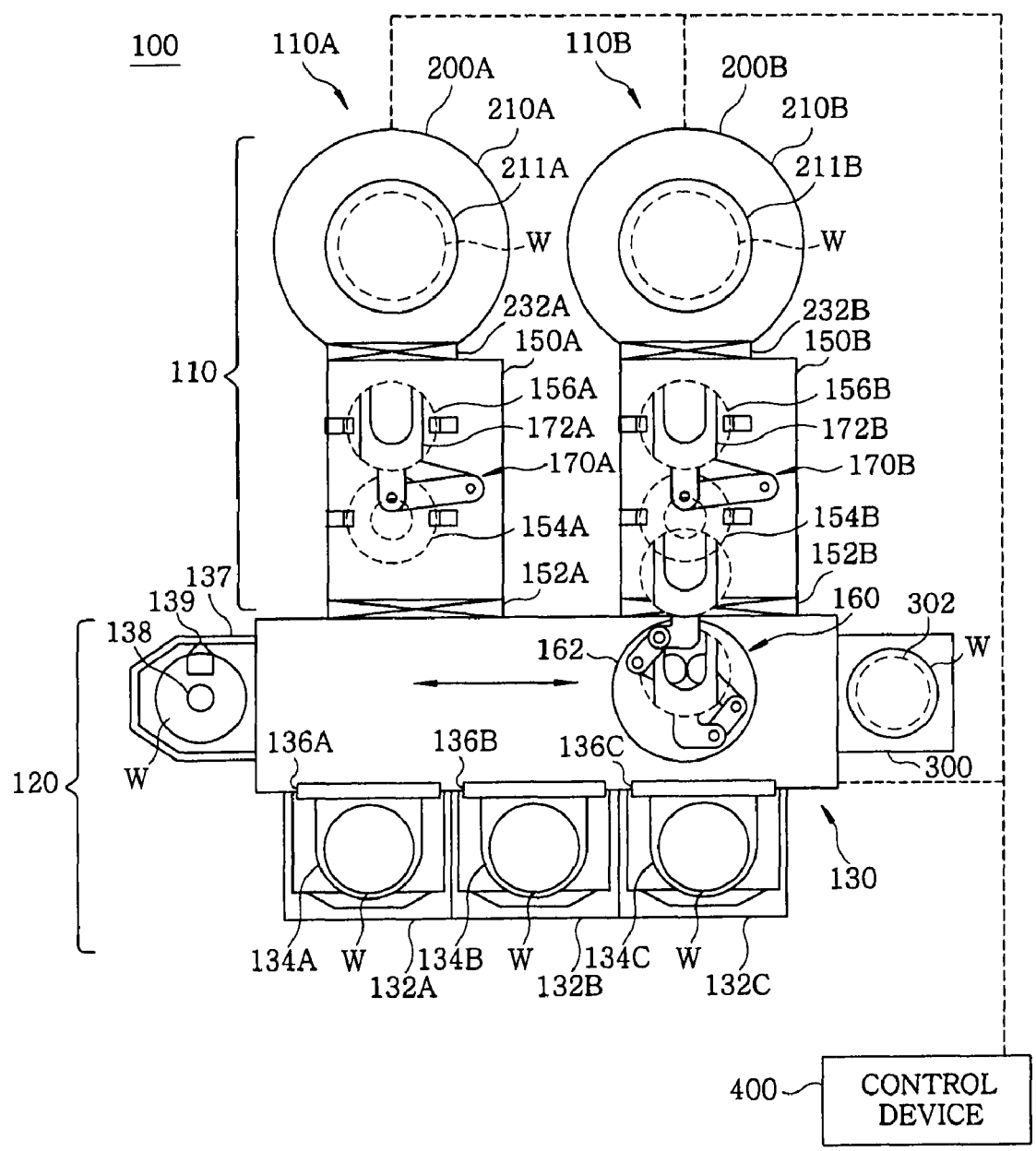
FIG. 1 is a schematic cross-sectional view showing a structure of a substrate processing apparatus in accordance with an embodiment of the present invention.

An embodiment of the present invention will be now described with reference to the accompanying drawings which form a part hereof.

Further, in the following description and drawings, components having substantially the same configuration and function are denoted by like reference characters, and thus redundant description thereof will be omitted herein.

(Example of Structure of Substrate Processing Apparatus)

Firstly, an example of a structure of a substrate processing apparatus in accordance with the embodiment of the present invention will be described with reference to FIG. 1. For example, a substrate processing apparatus having a transfer chamber to which at least one vacuum processing unit is connected is used in the present embodiment. FIG. 1 is a schematic cross-sectional view showing a structure of a substrate processing apparatus 100 in accordance with the embodiment of the present invention.

The substrate processing apparatus 100 includes one or two or more vacuum processing units (process ships) 110 performing a predetermined processing (e.g., etching process) on, e.g., a semiconductor wafer W and a transfer unit 120 loading and unloading the wafer W on and from the vacuum processing unit 110. The transfer unit (loader unit) 120 includes a transfer chamber 130 commonly used when the wafer W is transferred.

FIG. 1 shows, e.g., two vacuum processing units (process ships) 110A and 110B are arranged at a side portion of the transfer unit 120. The vacuum processing units 110A and 110B include plasma processing devices 200A and 200B and load-lock chambers 150A and 150B, respectively. The load-lock chambers 150A and 150B are connected to the plasma processing devices 200A and 200B, respectively, and function as relay chambers configured to perform vacuum evacuation. The vacuum processing units 110A and 110B perform a same type processing, e.g., etching process on the wafer W in the plasma processing devices 200A and 200B, respectively.

For example, the plasma processing devices 200A and 200B include processing chambers 210A and 210B, respectively, having susceptors (lower electrodes) 211A and 211B serving as mounting tables for mounting wafers therein and each of them performs a plasma etching process on the surface of a wafer by supplying a high frequency power to the susceptor 211A or 211B and a processing gas to the processing chamber 210A or 210B to be converted to plasma.

As shown in FIG. 1, the substrate processing apparatus including two vacuum processing units having plasma processing devices has hitherto been described, but the present invention is not limited to this embodiment. Alternatively, the substrate processing apparatus may include one or three or more vacuum processing units. Moreover, all the vacuum processing units need not have plasma processing devices installed. For example, the substrate processing apparatus may include some vacuum processing units having plasma processing devices and the other vacuum processing units having other processing devices (e.g., heat treating devices).

The transfer chamber 130 of the transfer unit 120 has a cross section of an approximately rectangular shape in which clean air or nonreactive gas such as $N_2$ gas circulates. A plurality of cassette stages 132A to 132C is installed in one longer side of the approximately rectangular shape of the cross section of the transfer chamber 130. Cassette containers 134A to 134C are mounted in the cassette stages 132A to 132C, respectively. In a sidewall of the transfer chamber 130, three loading ports 136A to 136C as input ports of wafers W are installed corresponding to each of the cassette stages 132A to 132C.

FIG. 1 shows an example in which three cassette containers 134A to 134C are mounted on the cassette stages 132A to 132C, respectively. However, the numbers of the cassette stages and cassette containers are not limited to the example. One or two, or four or more cassette stages and cassette containers may be installed.

Each of the cassette containers 134A to 134C has a multi-staged structure in which the wafers W can be mounted and accommodated in a regular pitch by at least one lot (e.g., 25 sheets) and also has a sealed structure filled with, e.g., $N_2$ gas.

The transfer chamber 130 is configured to load and unload the wafer W on and from its inside through the loading ports 136A to 136C.

In the transfer chamber 130, there is installed a common transfer mechanism (atmospheric pressure side transfer mechanism) transferring the wafer W in a lengthwise direction (in an arrow direction in FIG. 1). The common transfer mechanism 160 is fixable on, e.g., a support plate 162. The support plate 162 is configured to slide on a guide rail (not shown) placed along the lengthwise direction at a center portion of the transfer chamber by, e.g., a linear motor driving mechanism. The common transfer mechanism 160 may be, e.g., a double arm mechanism having two picks as shown in FIG. 1 or a single arm mechanism having one pick.

Bases of the two load-lock chambers 150A and 150B are connected to the other longer side of the approximately rectangular shape of the cross section of the transfer chamber 130 through gate valves (atmospheric pressure side gate valves) 152A and 152B, respectively, which are configured to be opened and closed. Front ends of the load-lock chambers 150A and 150B are connected to the processing chambers 210A and 210B through gate valves (vacuum side gate valves) 232A and 232B, respectively, which are configured to be opened and closed.

In the load lock chambers 150A and 150B, there are installed a pair of buffer mounting tables 154A and 156A and a pair of buffer mounting tables 154B and 156B, respectively, which temporally hold the wafer W. Here, the buffer mounting tables 154A and 154B, closer to the transfer chamber 130, are called first buffer mounting tables, and the buffer mounting tables 156A and 156B, closer to the processing chambers 210A and 210B, are called second buffer mounting tables. Individual transfer mechanisms 170A and 170B having multijoint arms capable of contracting and extending, revolving and, elevating are placed between the buffer mounting tables 154A and 156A and between the buffer mounting tables 154B and 156B, respectively.

Picks 172A and 172B are installed at front ends, respectively, of the individual transfer mechanisms 170A and 170B. By using the picks 172A and 172B, it is possible to perform the receiving and transferring of the wafer W between the buffer mounting tables 154A and 156A and between the buffer mounting tables 154B and 156B, respectively. Moreover, the loading and unloading of the wafer W between the load-lock chambers 150A and 150B and the processing chambers 210A and 210B is performed by using the individual transfer mechanisms 170A and 170B, respectively.

An orientor (pre-alignment stage) 137 serving as a pointing device of the wafer W is installed in one shorter side of the approximately rectangular shape of the cross section of the transfer chamber 130. The orientor 137, which includes, e.g., a rotation table 138 and an optical sensor 139, optically monitoring a peripheral portion of the wafer W, detects an orientation flat, notch or the like of the wafer W to perform position alignment.

A measuring chamber 300 is installed in the other shorter side of the approximately rectangular shape of the cross section of the transfer chamber 130. The measuring chamber 300, which is, e.g., a monitor (metrology) of an optical system, includes a mounting table 302 for mounting a transferred wafer W therein. The measuring chamber 300 obtains optical constants of a film formed on the wafer W that is mounted in the mounting table 302 or examines a line groove and a film thickness of a surface layer, a critical dimension (CD) of a gate electrode, and the like. An example of a structure of the measuring chamber 300 will be described below.

The substrate processing apparatus 100 includes: a control device 400 controlling operations of the aforementioned each element of vacuum processing units 10A and 110B and the transfer unit 120; and a manipulation unit (not shown) connected to the control device 400. In the manipulation unit, there is installed an operation panel and the like of a touch panel having a display unit such as, e.g., a liquid crystal display (LCD) or the like. The display unit displays an operation status of each element of the substrate processing apparatus 100. Moreover, a user can perform various manipulations of the substrate processing apparatus 100 by using the operation panel.

The control device 400 is configured to execute a predetermined program based on data such as a preset recipe and the like by the manipulation of the manipulation unit and to control each element of the vacuum processing units 110A and 110B and the transfer unit 120, e.g., the plasma processing devices 200A and 200B, the measuring chamber 300, the orientor 137, the transfer mechanisms 160 and 170, and the like. Accordingly, except for, e.g., the transferring of wafers and the processing (e.g., etching) of wafers, various measuring processes such as obtaining processes of optical constants of films formed on the wafers, re-obtaining processes, examining processes of film structures formed on the wafers, which will be described below, are performed.

(Example of Structure of Control Device)

Figure 2:
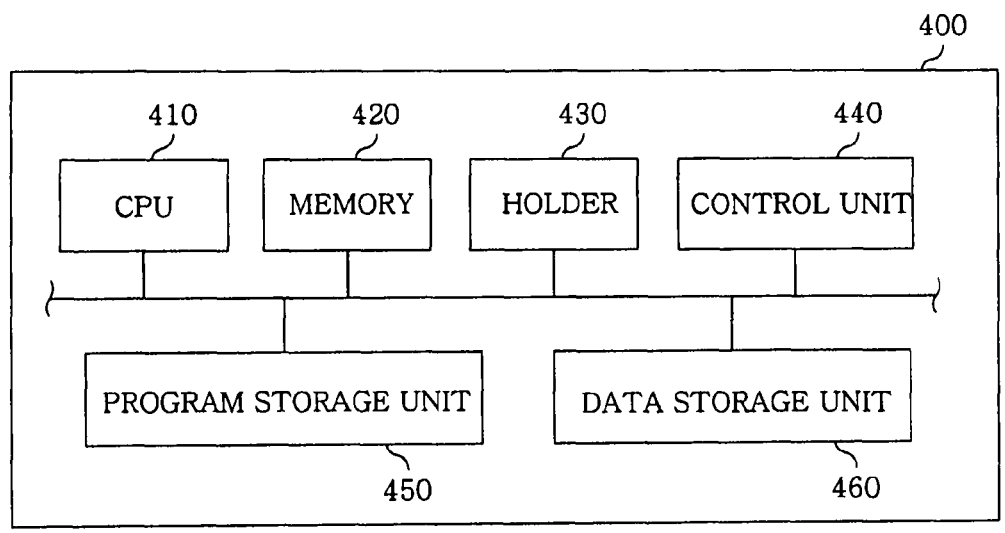
FIG. 2 is a block diagram showing an example of a structure of a control device shown in FIG. 1.

An example of a structure of the control device 400, controlling the transferring of wafers, in accordance with the present embodiment will be described with reference to FIG. 2. The control unit 400, e.g., as shown in FIG. 2, includes: a central processing unit (CPU) 410 forming its body; a memory 420 having a random access memory (ROM), a read only memory (ROM), and the like used by the CPU; a holder 430 having an alarm, e.g., a buzzer, or the like; a control unit 440 having various kinds of controller controlling each element of the substrate processing apparatus 100; a program storage unit 450 storing a program that executes the processing of the substrate processing apparatus 100; and a data storage unit 460 storing various data such as recipe data and the like to be used to execute the program-based processing. The program storage unit 450 and the data storage unit 460 are formed as storage mediums such as, e.g., flash memories, hard disks, CD-ROMS, and the like. Data in the program storage unit 450 and the data storage unit 460 are read by the CPU 410 as necessary.

The CPU 410, the memory 420, the control unit 440, the program storage unit 450, and the data storage unit 460 are electrically connected through bus lines such as control bus, system bus, data bus, and the like.

The control unit 440 includes various kinds of controllers controlling each element of the vacuum processing unit 110A and 110B, and the transfer unit 120, e.g., the plasma processing devices 200A and 200B, the measuring chamber 300, the orientor 137, the transfer mechanisms 160 and 170, and the like.

The program storage unit 450 stores a program for transferring a wafer, a program for performing a processing of a wafer such as etching, film formation, or the like, a program for examining a film structure of a wafer, and the like in addition to an obtaining process and a re-obtaining process of optical constants which will be described later.

The data storage unit 460 stores spectrums of reflectance, parameters, and obtained optical constants, which are necessary to execute the obtaining process and the re-obtaining process of optical constants. Further, the data storage unit 460 stores: a process recipe having data necessary to control each element for the transferring of a wafer; setting data (e.g., pressure inside the process chamber, kinds of gas, gas flow rate, high frequency power, and the like) necessary to control each element for the process; and an optical model necessary to perform an examining process on a film structure of a wafer; and the like.

(Example of Structure of Measuring Chamber)

Figure 3:
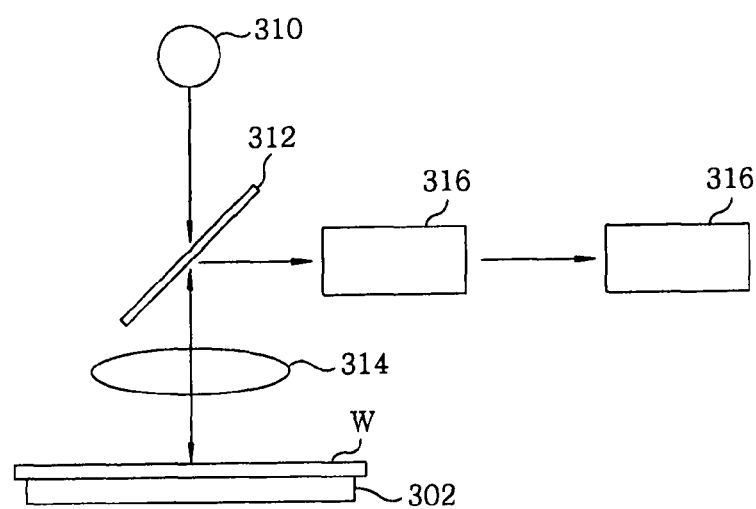
FIG. 3 schematically shows a structure of a measuring chamber shown in FIG. 1.

An example of an internal structure of the measuring chamber 300 will be described with reference to FIG. 3. FIG. 3 schematically shows a structure of a measuring chamber 300. The measuring chamber 300 in FIG. 3, which observes a reflection beam reflected from a surface of the wafer W mounted on the mounting table 302, is configured to function as a structure distinguishing device that examines a surface structure of the wafer W by using the spectral reflectance measuring method as one of the scatterometry. The spectral reflectance measuring method refers to a shape examining method that examines the surface structure of the wafer W, e.g., a film thickness, a CD value of a trench, and/or the like by emitting a white beam of light to the wafer W and measuring a reflectance (spectral reflectance intensity ratio), which is a ratio of intensity of an incident beam for each wavelength incident on the wafer W to intensity of a reflection beam reflected from the wafer W.

As shown in FIG. 3, in the measuring chamber 300, a white beam irradiated from a light source 310 is transmitted through a half mirror 312 and concentrated by a concentrating lens 314 toward the wafer W. The incident white beam is reflected from a surface of the wafer W. A path of a reflection beam reflected from the surface of the wafer W is changed by the half mirror 312 to travel to a spectrometer 316. The reflection beam is separated into its spectral components by the spectrometer 316. Such component beams are detected in a detector 318.

Accordingly, the control device 400 receives the intensity of the beams for the detected wavelengths to measure the spectral reflectance (spectral reflectance intensity ratio) and obtain and store the spectrum of the spectral reflectance. In detail, for example, the control device 400 performs predetermined calculations for an actually measured spectrum of the spectral reflectance, a theoretical spectrum, fitting of the spectrums, and the like. The control device 400 also stores predetermined program data and necessary data such as spectral data, optical constants of films, parameters for obtaining the optical constants, and the like.

The control device 400 examines the surface structure (film thickness, CD value, and the like) of the wafer W based on the spectrum of the spectral reflectance. In detail, for example, when a film thickness of a target object, i.e., a film structure is examined, optical models (spectrums of the spectral reflectance) corresponding to various film thicknesses of the target are obtained in advance and stored in the data storage unit 460. When a film structure of the wafer W is examined, the film structure is examined by emitting a beam to a target object, i.e., the film structure of the wafer W, to measure a spectral reflectance from a reflection beam of the beam and determining the thickness of the target by selecting an optical model (a spectrum of the spectral reflectance) of a thin thickness best matching to the spectrum of the spectral reflectance measured. The surface structure of the wafer W examined by the control device 400 is not limited to the film thickness. The control device 400 may examine, e.g., a CD value, depth, gradient, and/or the like of a trench formed on a surface of the wafer W.

However, the aforementioned optical model used to examine the surface structure of the wafer W is typically created by using optical constants, e.g., a refractive index n and an attenuation constant k of each film of the film structure of the wafer W. Accordingly, it is essential to accurately acquire the optical constants n and k of each film before the optical model is created.

In the present embodiment, optical constants n and k of each target film are obtained by a fitting to a spectrum of a spectral reflectance that is acquirable by using a film structure sample in which the target films are formed. In the fitting to the spectrum, a reflectance of each wavelength is first obtained from a reflection beam of a beam emitted to the film structure sample and an actually measured spectrum I of a spectral reflectance is acquired. In the meantime, for the same film structure sample, a reflectance of each wavelength is calculated by using an optical theoretical equation and a theoretical spectrum S of a spectral reflectance is acquired. The theoretical spectrum S is fitted to the an actually measured spectrum I and the optical constants n and k are obtained as optimized values to minimize a difference between the spectrums S and I.

Figure 4:
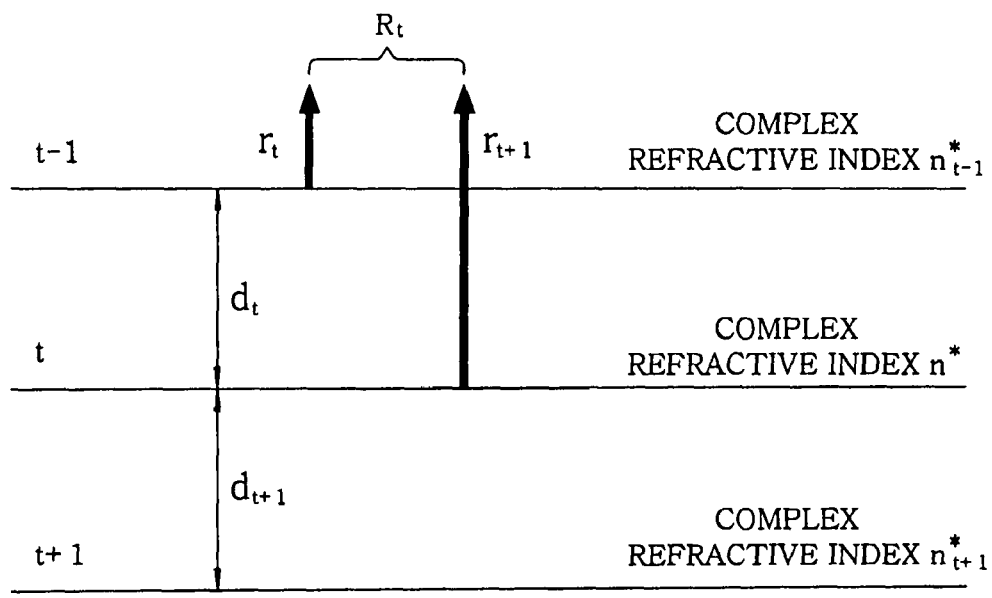
FIG. 4 shows a film-stacked structure for describing how a theoretical spectrum is calculated by using a theoretical equation.

An example of the theoretical equation for acquiring the theoretical spectrum S will be now described. In a film-stacked structure shown in FIG. 4, if optical constants of a target film, i.e., a $t^{th}$ film are obtained, a reflection beam $R_t$ of each wavelength $\lambda$ from the $t^{th}$ film is acquired by the following Eq. 1:

$$R_t = \frac{r_t + r_{t+1}\exp(-4\pi i n_t^* d_t/\lambda)}{1 + r_t r_{t+1}\exp(-4\pi i n_t^* d_t/\lambda)} \text{ and } \quad \text{Eq. 1}$$

$$r_t = \frac{n_t^* - n_{t-1}^*}{n_t^* + n_{t-1}^*}$$

where $R_t$ is the reflectance from the $t^{th}$ film; $R_{t+1}$ is the reflectance from a $t+1^{th}$ film; $D_t$ is a film thickness of the $t^{th}$ film; and $n^*_{t-1}$, $n^*_t$, and $n^*_{t+1}$ are complex refractive indexes, respectively. The complex refractive index $n^*_t$ may be represented by the following Eq. 2:

$$n^* = n - ik \quad \text{Eq. 2}$$

As a result, the reflectance $R_t$ can be calculated by using the film thickness and the optical constants of each film in accordance with the Eq. 1 and Eq. 2. Accordingly, the theoretical spectrum S $(=|R_t|^2)$ of the reflectance of the target film can be acquired.

The optical constants n and k may be represented as a plurality of parameters by using a dispersion equation. As examples of the dispersion equation, the optical constants n and k are represented as a wavelength $n^{th}$-order polynomial like a Cauchy equation that is used for the dispersion of a transparent medium or as a vibrator model that is used for an absorbing medium. Even though any dispersion equation is usable, the following Eq. 3 is employed as an example in the present embodiment. The Eq. 3 is a dispersion equation represented as a harmonic vibrator model that is acquirable from wave dependency of a dielectric constant of a material in the present embodiment.

$$n - ik = 1 + \frac{q_e^2}{2\varepsilon_0 m} \sum_j \frac{N_j}{\omega_j^2 - \omega^2 + i\gamma_j\omega} \quad \text{Eq. 3}$$

where $\varepsilon_0$ is a dielectric constant of vacuum; $q_e$ is a charge amount of an electron; m is a mass of an electron; $\omega$ is a natural frequency of an electric field; $\omega_j$ is an angular natural frequency of a $j^{th}$-order electron; $\gamma_j$ is a vibration damping coefficient of a $j^{th}$-order electron; and $N_j$ is the number of electrons having the angular natural frequency $\omega_j$ in a unit volume. Here, $\varepsilon_0$, $q_e$, and m are known constants. Accordingly, $\omega_j$, $\gamma_j$, and $N_j$ are considered as unknown parameters (fitting parameters) for optimization of the fitting. A film thickness $d_t$ is also acquired in the present embodiment. Accordingly, the parameters for the optical constants $\omega_j$, $\gamma_j$, and $N_j$ are alternatively called optical constant parameters to distinguish them from the film thickness $d_t$.

As such, optical constants of complex refractive indexes of each film (($t-1)^{th}$ film, $t^{th}$ film, and $(t+1)^{th}$ film) can be represented by using the optical constant parameters in accordance with the Eq. 2 and the Eq. 3. Accordingly, it is possible to represent the reflectance $R_t$ for each wavelength by use of the optical constant parameters of each film by putting the optical constant parameters into the Eq. 1.

For the fitting of spectrums, e.g., the optical constant parameters $\omega_j$, $\gamma_j$, and $N_j$ of the target film by the Eq. 3 and the film thickness $d_t$ are provided as fitting parameters and the other parameters are fixed by using, e.g., a previously acquired value and a literature value in order to acquire optimized values of the fitting parameters. In other words, a combination of the fitting parameter values is acquired by varying the fitting parameters to minimize a difference between the theoretical spectrum S and the actually measured spectrum I.

In the present embodiment, e.g., a square sum of errors (SSE) between the theoretical spectrum S and the actually measured spectrum I is calculated as the difference therebetween by varying the parameters and the optical constants n and k are obtained, by using the Eq. 2, from a combination of the parameters to minimize the square sum of errors therebetween. As such, in accordance to the present embodiment, the square sum of errors between the spectrums S and I is calculated as the difference therebetween. The present invention, however, is not limited to this embodiment. For example, mean squared error (MSE) may be calculated.

In the optical constant parameters $\omega_j$, $\gamma_j$, and $N_j$, j is a natural number and the number of parameters is variable depending on a value of j. The value of j depends on the kinds of films. When optical constants of, e.g., a polysilicon film of the wafer W are obtained, the value of j ranges from 0 to 6. In this case, the optical constant parameters are $\omega_0$ to $\omega_6$, $\gamma_0$ to $\gamma_6$, and $N_0$ to $N_6$. When optical constants of an oxide film formed on the polysilicon film are obtained, the value of j ranges from 0 to 1. In this case, the optical constant parameters are $\omega_0$ to $\omega_1$, $\gamma_0$ to $\gamma_1$, and $N_0$ to $N_1$. Moreover, when optical constants of a BARC film formed on the oxide film and a photoresist film formed on the BARC film, respectively, are obtained, each of the values of j ranges from 0 to 6.

(Example of Film Structure, Optical Constants of which will be Obtained)

Figure 5:
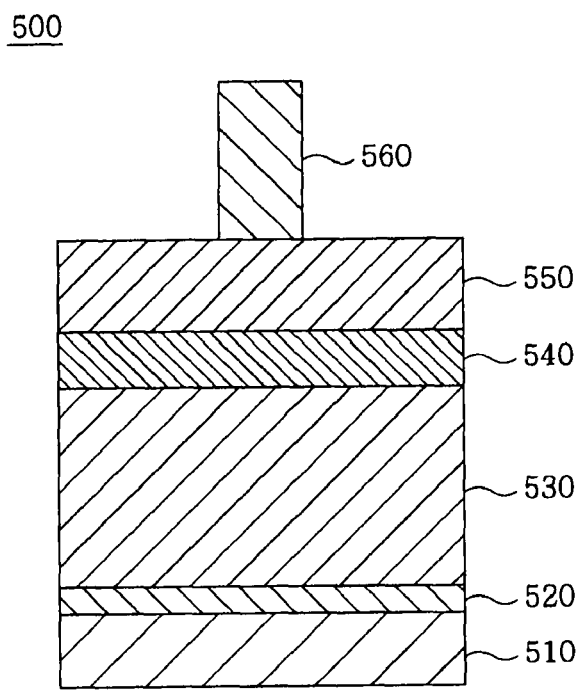
FIG. 5 shows an example of a film-stacked structure on a surface of a wafer on which a plurality of films for measuring their optical constants is stacked.

Next, an example of a film-stacked structure including a plurality of films stacked therein, optical constants of which will be obtained, formed on a surface of the wafer W will be described with reference to FIG. 5. FIG. 5 is a schematic cross-sectional view showing a film-stacked structure 500 formed on a surface of the Wafer W. In the film-stacked structure 500 in FIG. 5, a gate oxide film 520, a polysilicon film 530, an oxide film 540, a BARC film 550, and photoresist film 560 are stacked on a silicon substrate in that order. For example, an opening is patterned on the photoresist film 560. Since the plasma processing devices 200A and 200B perform an etching process on the wafer W, the BARC film 550 and the photoresist film 560 are removed and, e.g., a groove (a trench) is formed on the polysilicon film 530.

To obtain optical constants of each film of the film-stacked structure 500, a film structure sample in which a target sample film is located at a top is used for each of the films. The target sample film corresponds to a target film, optical constants of which will be obtained. A film structure of the target sample film and sample films located below the target sample film in the film structure sample is identical to that of the target film and below-located films located below the target film in the film-stacked structure 500. For example, as shown in FIG. 6, when optical constants $n_1$ and $k_1$ of a target film, i.e., the polysilicon film 530 is obtained, a film structure sample A in which a gate oxide film 520a, and a target sample film, i.e., a polysilicon film 530a are stacked on a silicon substrate 510a from bottom to top in that order is used.

When optical constants $n_2$ and $k_2$ of the oxide film 540 is obtained, a film structure sample B in which a gate oxide film 520b, a polysilicon film 530b, and an oxide film 540b are stacked on a silicon substrate 510b from bottom to top in that order is used. Moreover, when optical constants $n_3$ and $k_3$ of the BARC film 550 is obtained, a film structure sample C in which a gate oxide film 520c, a polysilicon film 530c, an oxide film 540c, and a BARC film 550c are stacked on a silicon substrate 510c from bottom to top in that order is used.

When optical constants $n_4$ and $k_4$ of the photoresist film 560 is obtained, a film structure sample D in which a gate oxide film 520d, a polysilicon film 530d, an oxide film 540d, a BARC film 550d, and a photoresist film 560d are stacked on a silicon substrate 510d from bottom to top in that order is used.

The film structure samples A to D are individually generated on a plurality of wafers W. In this case, it is preferable to use wafers W having same kinds of sample films as the films of the film-stacked structure 500 in which the sample films are removed in an etch back process. However, the present invention is not limited to such a method. It may be possible to employ wafers W in which the sample films are formed for the film structure samples A to D.

Actually measured spectrums $I_A$ to $I_D$ of the film structure samples A to D may be acquired by using the aforementioned substrate processing apparatus 100. For example, when the actually measured spectrum $I_A$ of the film structure sample A is acquired, under the control of the control device 400, a wafer W formed with the film structure sample A is transferred to the measuring chamber 300, and a beam is emitted to a surface of the film structure sample A and a reflection beam of the beam is measured to acquire a reflectance for each wavelength, thereby acquiring the actually measured spectrum $I_A$ of a spectral reflectance. The actually measured spectrums $I_A$ to $I_D$ may be acquired and stored in the data storage unit 460 whenever optical constants of each film are obtained. Alternatively, the measured spectrums $I_A$ to $I_D$ may be acquired and stored in the data storage unit 460 before the optical constants of each film are obtained.

Further alternatively, the measured spectrums $I_A$ to $I_D$ may be obtained by transferring one wafer W to the measuring chamber 300 whenever one film is formed on the wafer W in the process in which films are formed successively on a bottom of the wafer W.

(Basic Process of Obtaining Optical Constants)

Basic process of obtaining optical constants of each film of the film-stacked structure 500 will be described. Each of the films of the film-stacked structure 500 is determined as the target film from bottom to top. Optical constants of the target films are successively obtained by executing the basic process including a fitting to spectrums of a spectral reflectance.

In this case, all of the optical constants including that of a lowest film of the wafer W need not be calculated. For example, in the present embodiment, since the lowest film, i.e., the gate oxide film 520 is of a very thin thickness than other films and is located below the polysilicon film 530 having a high refractive index, its influence on the reflectance of other films is small. Accordingly, for the optical constants of the gate oxide film 520, a literature value or an already measured value may be used.

Accordingly, in the present embodiment, the optical constants of the gate oxide film 520 are fixed as well-known values and optical constants of the polysilicon film 530, which is located on the gate oxide film 520, as a first target film are obtained. Then, optical constants of the oxide film 540, the BARC film 550, and the photoresist film 560 as next target films are successively calculated in that order.

An example of the basic process that obtains the optical constants of each film by a fitting to spectrums of a spectral reflectance by using the film structure samples A to D will be now described with reference to FIG. 7. The fitting for a target sample film is performed by the control device 400 based on, e.g., the flowchart in FIG. 7. As described above, for the film structure sample A, the optical constants of the gate oxide film 520a are fixed as the well-known values and the optical constants $n_1$ and $k_1$ of the polysilicon film 530a are obtained. The same is successively applicable to the optical constants of the other sample top films.

Generally, an actually measured spectrum I of a spectral reflectance is firstly acquired by using a film structure sample having a top sample film as a target sample film and is stored in the data storage unit 460 (S110). By determining a set of parameters by the aforementioned theoretical equation, a theoretical spectrum S of a spectral reflectance of the film structure sample can be obtained (S120). In detail, when the target sample film is the polysilicon film 530a, an actually measured spectrum $I_A$ of a spectral reflectance is acquired by using a film structure sample A shown in FIG. 6 and an actually measured spectrum $I_A$ is stored. A theoretical spectrum $S_A$ of the spectral reflectance is calculated based on the theoretical equation. In the theoretical spectrum $S_A$, the optical constants $n_{1a}$ and $k_{1a}$ of the polysilicon film 530a are acquired by providing 21 optical constant parameters $P_1$ ($\omega_j$, $\gamma_j$, and $N_j$ (J=0 to 6)) as fitting parameters. Moreover, a film thickness $d_{A1}$ of the polysilicon film 530a is acquired as the fitting parameter together with the 21 optical constant parameters $P_1$. As a result, the number of fitting parameters becomes 22. Then, the theoretical spectrum S is fitted to the actually measured spectrum I and a combination of the parameters that minimizes a difference between the spectrums S and I is acquired and stored in the data storage unit 460 (S130). Optical constants of the target sample film are obtained from the acquired combination of parameters and stored in the data storage unit 460 (S140). In detail, the theoretical spectrum $S_A(P_1$ and $d_{A1})$ is fitted to the actually measured spectrum $I_A$ by varying the fitting parameters $P_1$ and $d_{A1}$. Accordingly, the optical constants $n_1$ and $k_1$ of the polysilicon film 530a are obtained from a combination of the parameters acquired to minimize a difference between the theoretical spectrum $S_A$ and the actually measured spectrum $I_A$ (a square sum of errors in the present embodiment) and the acquired combination of the parameters and the optical constants $n_{1a}$ and $k_{1a}$ are stored. Next, optical constants $n_{2b}$ and $k_{2b}$ of the oxide film 540b are obtained by using the fitting operation in FIG. 7. In accordance with the fitting operation described in FIG. 7, an actually measured spectrum $I_B$ of a spectral reflectance is acquired by using the film structure sample B and the actually measured spectrum $I_B$ is stored (S110). A theoretical spectrum $S_B$ of the spectral reflectance is calculated based on the theoretical equation (S120). At the time when the theoretical spectrum $S_B$ is calculated, optical constants of the polysilicon film 530b that is located below the oxide film 540b have already been obtained. Accordingly, in the theoretical spectrum $S_B$, the optical constants of the polysilicon film 530b are fixed as previously obtained parameter values and all 8 parameters, i.e., 6 optical constant parameters $P_2$ ($\omega_j$, $\gamma_j$, and $N_j$ (J=0 and 1)) of the oxide film 540b, a film thickness $d_{B1}$ of the polysilicon film 530b, and a film thickness $d_{B2}$ of the oxide film 540b are used as fitting parameters. Then, the theoretical spectrum $S_B(P_2, d_{B1}$ and $d_{B2})$ is fitted to the actually measured spectrum $I_A$ by varying the fitting parameters $P_2$, $d_{B1}$ and $d_{B2}$. Accordingly, a combination of the parameters is acquired to minimize a difference between the theoretical spectrum $S_B$ and the actually measured spectrum $I_B$ (a square sum of errors in the present embodiment) and the acquired combination of the parameters is stored (S130). Then, the optical constants $n_{2b}$ and $k_{2b}$ of the oxide film 540b are obtained from the acquired combination of the parameters and the obtained optical constants $n_2$ and $k_2$ are stored (S140).

Figure 7:
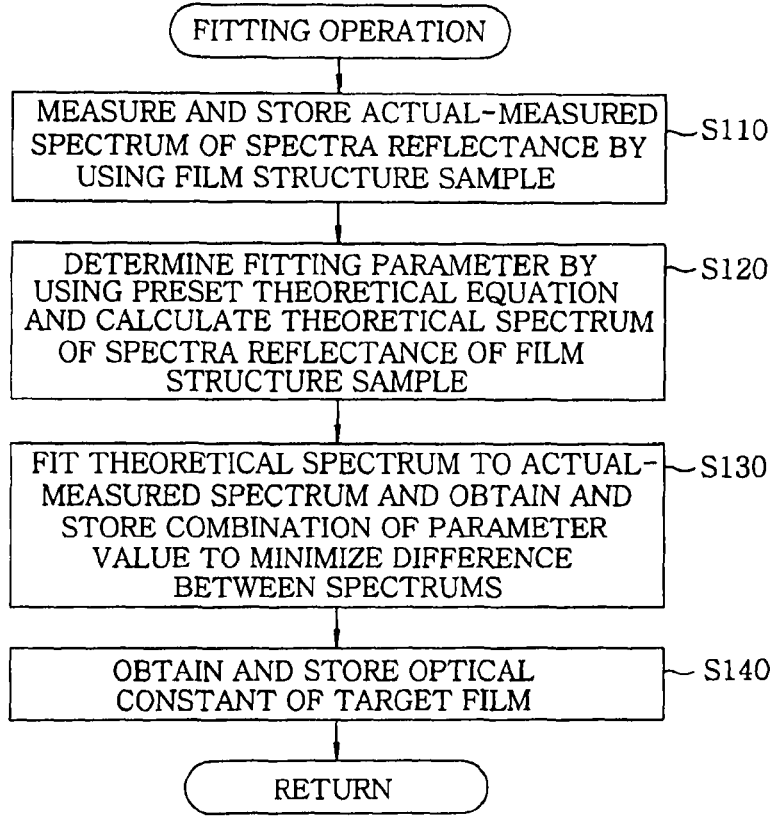
FIG. 7 is a flowchart showing an example of a fitting operation of a basic process in accordance with the embodiment of the present invention.

Similarly, in accordance with the fitting operation in FIG. 7, optical constants $n_{3c}$ and $k_{3c}$ of the BARC film 550c and optical constants $n_{4d}$ and $k_{4d}$ of the photoresist film 560d are obtained by using the film structure sample C and the film structure sample D, respectively.

In detail, in order to obtain the optical constants $n_{3c}$ and $k_{3c}$ of the BARC film 550c, an actually measured spectrum $I_C$ of a spectral reflectance is acquired by using the film structure sample C and the actually measured spectrum $I_C$ is stored (S110). A theoretical spectrum $S_C$ of the spectral reflectance is calculated based on the theoretical equation (S120). At the time when the theoretical spectrum $S_C$ is calculated, optical constants of the polysilicon film 530c and the oxide film 540c that are located below the BARC film 550c have been already obtained. Accordingly, in the theoretical spectrum $S_C$, the optical constants of the polysilicon film 530c and the oxide film 540c are fixed as previously obtained parameter values and optical constant parameters $P_3$ of the BARC film 550c, a film thickness $d_{C1}$ of the polysilicon film 530c, a film thickness $d_{C2}$ of the oxide film 540c, and a film thickness $d_{C3}$ of the BARC film 550c are used as fitting parameters. Then, the theoretical spectrum $S_C(P_3, d_{C1}, d_{C2},$ and $d_{C3})$ is fitted to the actually measured spectrum $I_A$ by varying the fitting parameters $P_3$, $d_{C1}$, $d_{C2}$, and $d_{C3}$. Accordingly, a combination of the parameters that minimizes a difference between the theoretical spectrum $S_C$ and the actually measured spectrum $I_C$ (a square sum of errors in the present embodiment) is acquired and the acquired combination of the parameters is stored. (S130) Then, the optical constants $n_{3c}$ and $k_{3c}$ of the BARC film 550c are obtained from the acquired combination of the parameters and the obtained optical constants $n_{3c}$ and $k_{3c}$ are stored (S140).

In order to obtain the optical constants $n_{4d}$ and $k_{4d}$ of the photoresist film 560d, an actually measured spectrum $I_D$ of a spectral reflectance is obtained by using the film structure sample D and the actually measured spectrum $I_D$ is stored (S110). A theoretical spectrum $S_D$ of the spectral reflectance is calculated based on the theoretical equation (S120). At the time when the theoretical spectrum $S_D$ is calculated, optical constants of the polysilicon film 530d and the oxide film 540d, the BARC film 550d have been already obtained. Accordingly, in the theoretical spectrum $S_D$, the optical constants of the polysilicon film 530d, the oxide film 540d, and the BARC film 550d are fixed as previously obtained parameter values and optical constant parameters $P_4$ of the photoresist film 560d, a film thickness $d_{D1}$ of the polysilicon film 530d, a film thickness $d_{D2}$ of the oxide film 540d, a film thickness $d_{D3}$ of the BARC film 550d, and a film thickness $d_{D4}$ of the photoresist film 560d are used as fitting parameters. Then, the theoretical spectrum $S_D(P_4, d_{D1}, d_{D2}, d_{D3},$ and $d_{D4})$ is fitted to the actually measured spectrum $I_D$ by varying the fitting parameters $P_4$, $d_{D1}$, $d_{D2}$, $d_{D3}$, and $d_{D4}$. Accordingly, a combination of the parameters that minimizes a difference between the theoretical spectrum $S_D$ and the actually measured spectrum $I_D$ (a square sum of errors in the present embodiment) is acquired and the acquired combination of the parameters is stored (S130). Then, the optical constants $n_{4d}$ and $k_{4d}$ of the photoresist film 560d are obtained from the acquired combination of the parameters and the obtained optical constants $n_{4d}$ and $k_{4d}$ are stored (S140).

In accordance with the basic process of the present embodiment, when the optical constants of each sample film are obtained from bottom to top, the fitting operation is performed after optical constants of a sample film(s) that is below a target sample film are fixed as a previously obtained parameter value(s). As such, when optical constants of a sample film(s) that is below the target sample film have already been obtained, it is possible to reduce the number of the parameters by obtaining optical constants of the target sample film by using the previously obtained optical constants of the sample film(s). Accordingly, it is possible to shorten the time required in the fitting operation.

However, in this case, it has been proved that even though the accuracy in the fitting operation is satisfactory when optical constants of a sample film(s) that is below a target sample film are obtained, the fitting operation may be unsatisfactorily performed when optical constants of the target sample film are obtained.

Figure 8:
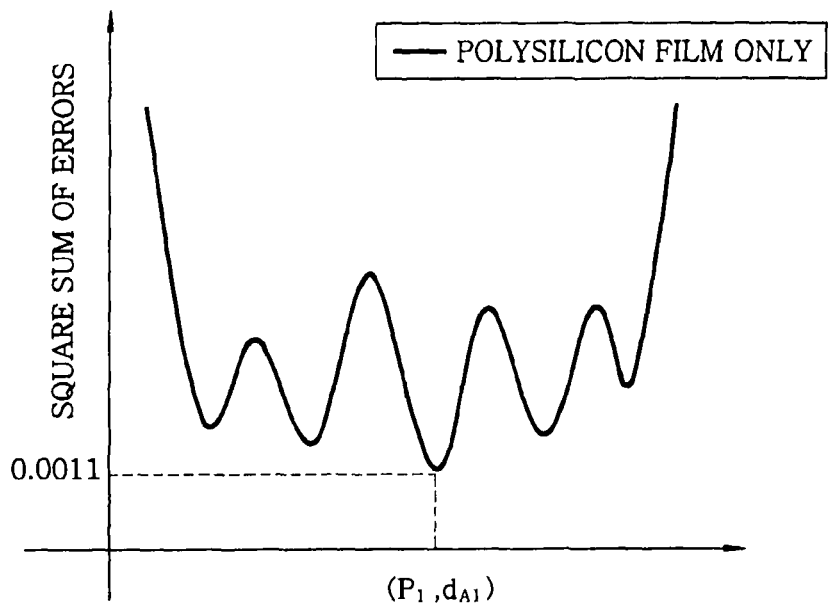
FIG. 8 is a two dimensional graph conceptually showing a square sum of errors between a theoretical spectrum and an actually measured spectrum in a fitting operation when optical constants of a target film, i.e., a poly silicon film are obtained in a basic process.
Figure 9:
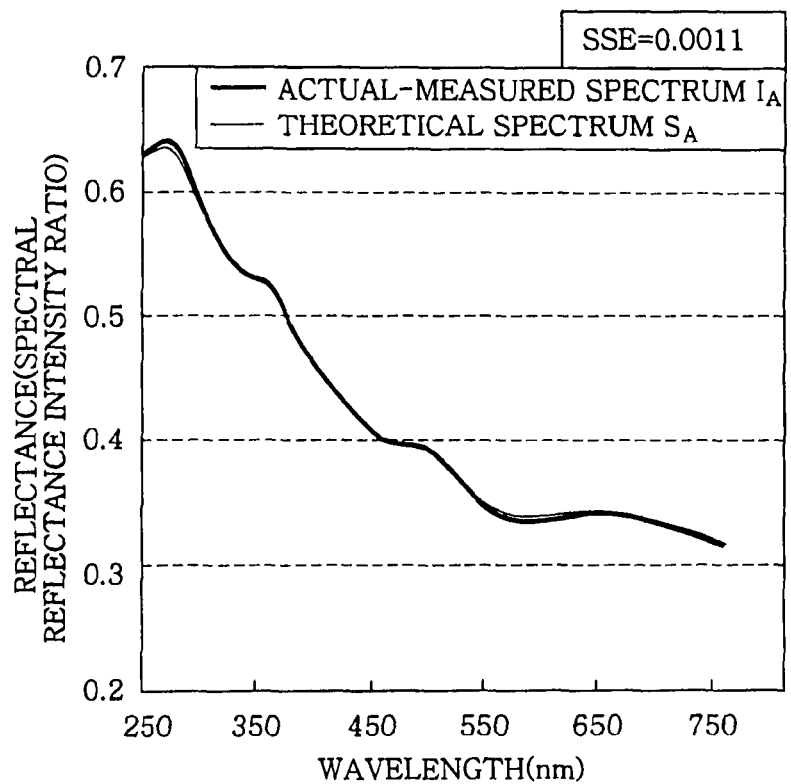
FIG. 9 is a graph showing a theoretical spectrum and an actually measured spectrum of a film structure sample A when the square sum of errors in FIG. 8 is minimized.

Hereinafter, such a case that the fitting operation may be unsatisfactorily performed will be described in detail with reference to the relative drawings. FIG. 8 is a graph showing a square sum of errors between the theoretical spectrum $S_A$ and the actually measured spectrum $I_A$ in the fitting operation when the optical constants $n_{1a}$ and $k_{1a}$ of the polysilicon film 530a as a target sample film are obtained. FIG. 9 is a graph showing the theoretical spectrum $S_A$ and the actually measured spectrum $I_A$, optimized when the square sum of errors in FIG. 8 is minimized.

Figure 10:
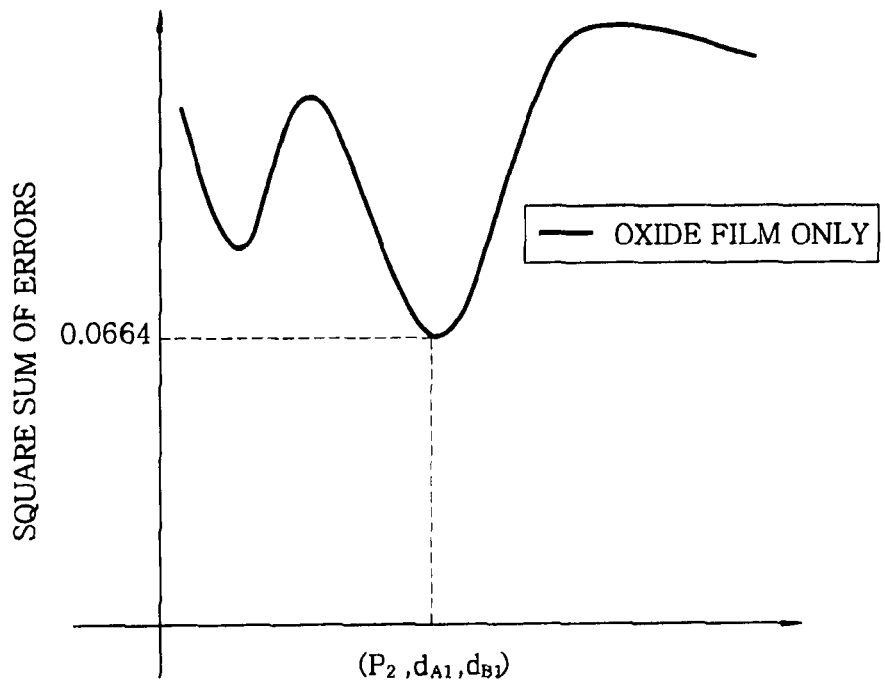
FIG. 10 is a two dimensional graph conceptually showing a square sum of errors between a theoretical spectrum and an actually measured spectrum in a fitting operation when optical constants of a target film, i.e., an oxide film are obtained in a basic process.
Figure 11:
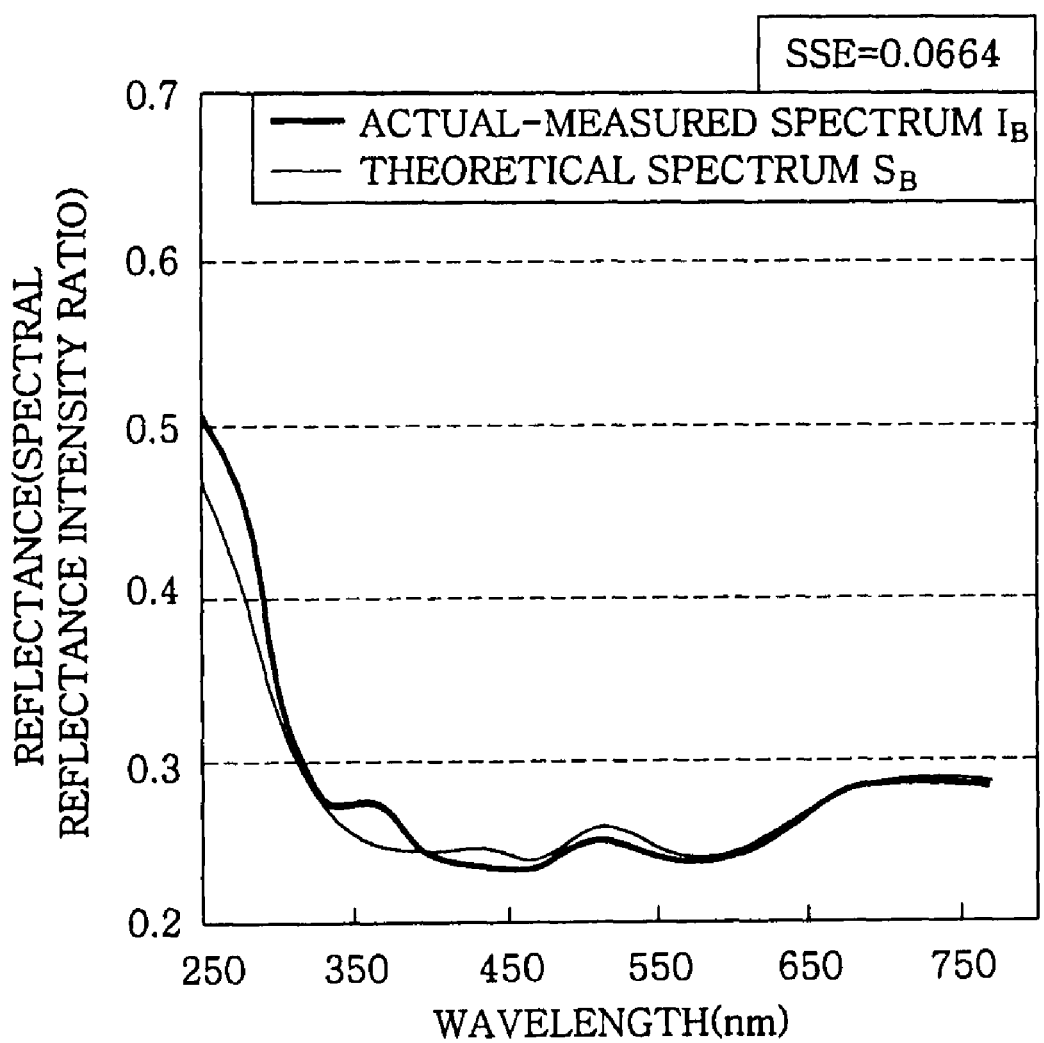
FIG. 11 is a graph showing a theoretical spectrum and an actually measured spectrum of a film structure sample B when the square sum of the errors in FIG. 10 is minimized.

FIG. 10 is a graph conceptually showing a square sum of errors between the theoretical spectrum $S_A$ and the actually measured spectrum $I_A$ in the fitting operation when the optical constants $n_{2b}$ and $k_{2b}$ of the oxide film 540b are obtained by using the optimized optical constants $n_1$ and $k_1$ of the polysilicon film 530a. FIG. 11 is a graph showing the theoretical spectrum $S_A$ and the actually measured spectrum $I_A$, optimized when the square sum of errors in FIG. 10 is minimized. In the case of the polysilicon film 530a and the oxide film 540b as the target objects, there are provided 22 and 8 parameters, respectively. Accordingly, although the dimensions of graphs in FIGS. 8 and 10 should have originally been 22 and 8, respectively, each of FIGS. 8 and 10 conceptually two-dimensionally shows the square sum of errors for easy understanding of images of the square sum of errors.

In the fitting of spectrums for the polysilicon film 530a as the target sample film, a minimum value of the square sum of errors between the theoretical spectrum $S_A$ and the actually measured spectrum $I_A$ is 0.0011 as shown in FIG. 8. At the time when the square sum of errors between the spectrums $S_A$ and $I_A$ has the minimum value of 0.0011, the theoretical spectrum $S_A$ and the actually measured spectrum $I_A$ are substantially identical to each other as shown in FIG. 9. This shows that the accuracy in the fitting is very satisfactory.

However, in the fitting of spectrums for the oxide film 540b as the target film, a minimum value of the square sum of errors between the theoretical spectrum $S_B$ and the actually measured spectrum $I_B$ is 0.0664 as shown in FIG. 10. This value of 0.0664 is 60 times greater than the value of 0.0011 shown in FIG. 8. Moreover, at the time when the square sum of errors between the spectrums $S_B$ and $I_B$ has the minimum value of 0.0664, the fitting of the spectrum $S_B$ and $I_B$ may be not satisfactory as shown in FIG. 11. Especially, the theoretical spectrum $S_A$ and the actually measured spectrum $I_A$ are significantly different from each other in a short wavelength region.

In this case, even if the fitting operation of the oxide film 540$b$ is repeated in plural times, it may be difficult to expect a satisfactory result of the fitting operation. It may be inferred that the used optical constants $n_{1a}$ and $k_{1a}$ of the polysilicon film 530$a$ are not physically correct.

Typically, a plurality of fitting parameters is varying and the more fitting parameters are varying, the more their combinations are created. Accordingly, there may be a plurality of local minimum solutions to bring about mathematically satisfactory results of the fitting of the theoretical spectrum S and the actually measured spectrum I. In this case, all the mathematically calculated answers are not physically correct. Therefore, when the optical constants of a sample film(s) that is located below a target film are not physically correct, it may be difficult to improve the accuracy in the fitting of spectrums of the target sample film by using the physically incorrect optical constants.

For that reason, in the present embodiment, optical constants of a target sample film are obtained by using optical constants of a below-located sample film(s) that is located below the target sample film in accordance with the basic process including the fitting, but if a satisfactory result of the fitting is not acquired, a re-obtaining process is performed. In the re-obtaining process, both of the optical constants of the target film and those of the below-located sample film(s) are re-obtained through a re-fitting operation. Since, by using the re-obtaining process, the optical constants of the below-located sample film(s) are correctable and the optical constants of the target film are re-calculable, the optical constants of the below-located sample film(s) may be corrected to physically correct values. Accordingly, it is possible to more efficiently improve the obtaining accuracy in the optical constants of the target sample film.

(Re-Obtaining Process to Correct Optical Constants)

Figure 12:
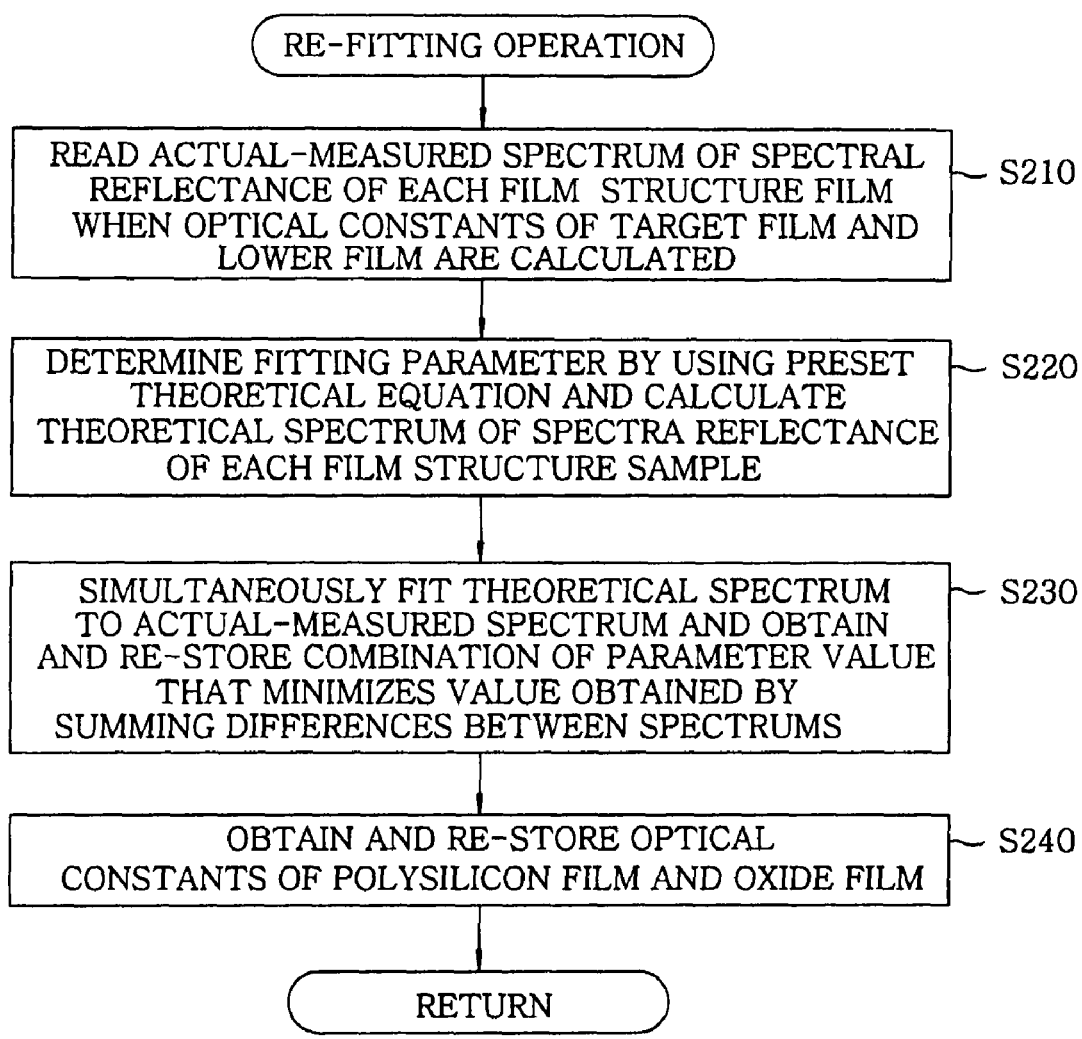
FIG. 12 is a flowchart showing an example of a re-fitting operation of a re-obtaining process in accordance with the embodiment of the present invention.

Next, an Example of the Re-Obtaining Process Including the re-fitting operation will be described with reference to FIG. 12. A re-fitting operation of a target sample film is performed by the control device 400 based on, e.g., the flowchart in FIG. 12. Below described is the case that the optical constants $n_{2b}$ and $k_{2b}$ of the oxide film 540$b$ as the target film and optical constants $n_{1b}$ and $k_{1b}$ of the polysilicon film 530$b$ located below the oxide film 540$b$ are corrected and re-obtained by using the re-fitting operation as an example.

First, actually measured spectrums of a spectral reflectance of each film structure sample when optical constants of the target sample film and optical constants of the below-located sample film are obtained are read (S210). Here, since the target sample film is the oxide film 540$b$ and the below-located sample film is the polysilicon film 530$b$, an actually measured spectrum $I_B$ of a spectral reflectance of the film structure sample B when optical constants $n_{2b}$ and $k_{2b}$ of the oxide film 540$b$ are obtained and an actually measured spectrum $I_A$ of the spectral reflectance of the film structure sample A when the optical constants $n_{1a}$ and $k_{1a}$ of the polysilicon film 530$a$ are obtained are read from the data storage unit 460.

Then, necessary fitting parameters are determined by using the theoretical equation and a theoretic spectrum of a spectral reflectance of each film structure sample is calculated (S220). The theoretical spectrum $S_A$ of the spectral reflectance of the film structure sample A to be fitted to the actually measured spectrum $I_A$ and the theoretical spectrum $S_B$ of the spectral reflectance of the film structure sample B to be fitted to the actually measured spectrum $I_B$ are calculated.

For the theoretical spectrum $S_A$, there are provided 22 fitting parameters including the optical constant parameters $P_1$ ($\omega_j$, $\gamma_j$, and $N_j$ (J=0 to 6)) and the film thickness $d_{A1}$ of the polysilicon film 530$a$. For the theoretical spectrum $S_B$, there are provided 29 fitting parameters including the optical constant parameters $P_2$ ($\omega_j$, $\gamma_j$, and $N_j$ (J=0 to 1)) and the film thickness $d_{B2}$ of the oxide film 540$b$ and further the optical constant parameters $P_1$ ($\omega_j$, $\gamma_j$, and $N_j$ (J=0 to 6)) and the film thickness $d_{B1}$ of the polysilicon film 530$b$.

At the time when the re-fitting operation is performed, a combination of the parameters that has already been calculated in the basic step of the fitting process shown in FIG. 7 is inputted as initial values of the fitting parameters. Accordingly, it is possible to approach to a minimum value more quickly a random value is inputted. Moreover, the time required in the re-fitting operation can be shortened.

Next, the theoretical spectrums are simultaneously fitted to the actually measured spectrums, respectively, for each of the film structure samples by putting a common value(s) into the optical constant parameter(s) of common films and varying the parameter(s). Then, a combination of the parameter values is acquired to minimize a value calculated by summing differences between the theoretical spectrums and the actually measured spectrums and the acquired combination is restored (S230). In other words, the fittings to the actually measured spectrum $I_A$ and the theoretical spectrum $S_A$($P_1$ and $d_{A1}$) for the film structure sample A and of the actually measured spectrum $I_B$ and the theoretical spectrum $S_B$($P_1$, $P_2$, $d_{B1}$, and $d_{B2}$) for the film structure sample B are simultaneously performed.

At the time when the fittings are simultaneously performed, a common value is inserted into the optical constant parameter $P_1$ of common sample films, i.e., the polysilicon films 530$a$ and 530$b$ of the film structure samples A and B. Then, the respective fitting parameters are varied to simultaneously perform each of the fittings. Accordingly, it is possible to increase the coincidence of the spectrums in the respective fittings, thereby improving the accuracy in the fittings.

As such, the fittings of the spectrums $I_A$ and $S_A$ and of the spectrums $I_B$ and $S_B$ are simultaneously performed and a combination of the parameters is acquired to minimize a value calculated by summing differences of the fittings. In other words, a combination of the parameters is acquired to minimize a value calculated by summing a square sum of errors between the spectrums $S_A$ and $I_A$ and a square sum of errors between the spectrums $S_B$ and $I_B$. Then, the optical constants of the polysilicon film 530$b$ and the oxide film 540$b$ are obtained from the calculated combination of the parameters and the obtained optical constants are modified. The modification of the calculated combination of the parameters and the obtained optical constants are performed by, e.g., rewriting the combination and the optical constants at positions where certain values have been already written in the data storage unit 460.

Figure 13:
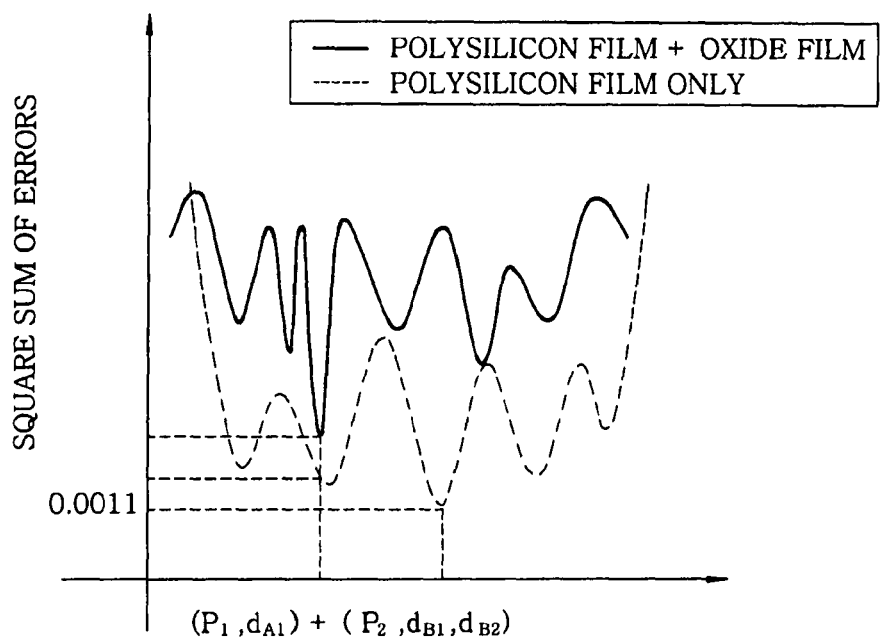
FIG. 13 is a two-dimensional graph that conceptually shows a summation of each square sum of errors when fittings of each spectrum are simultaneously performed in a re-obtaining process.

FIG. 13 is a two-dimensional graph that conceptually shows the square sum of errors when the fittings to the spectrums $S_A$ and $I_A$ and the spectrums $S_B$ and $I_B$ are simultaneously performed (re-obtaining process). In FIG. 13, the value calculated by summing the square sum of errors between the spectrums $S_A$ and $I_A$ and the square sum of errors between the spectrums $S_B$ and $I_B$ is represented as a curve of a solid line. Further, for the comparison, the curve showing the square sum of errors between the spectrums $S_A$ and $I_A$ when only the fitting of the spectrums $S_A$ and $I_A$ are performed (basic process) as shown in FIG. 8 is represented by using a dashed line in FIG. 13.

Figure 14:
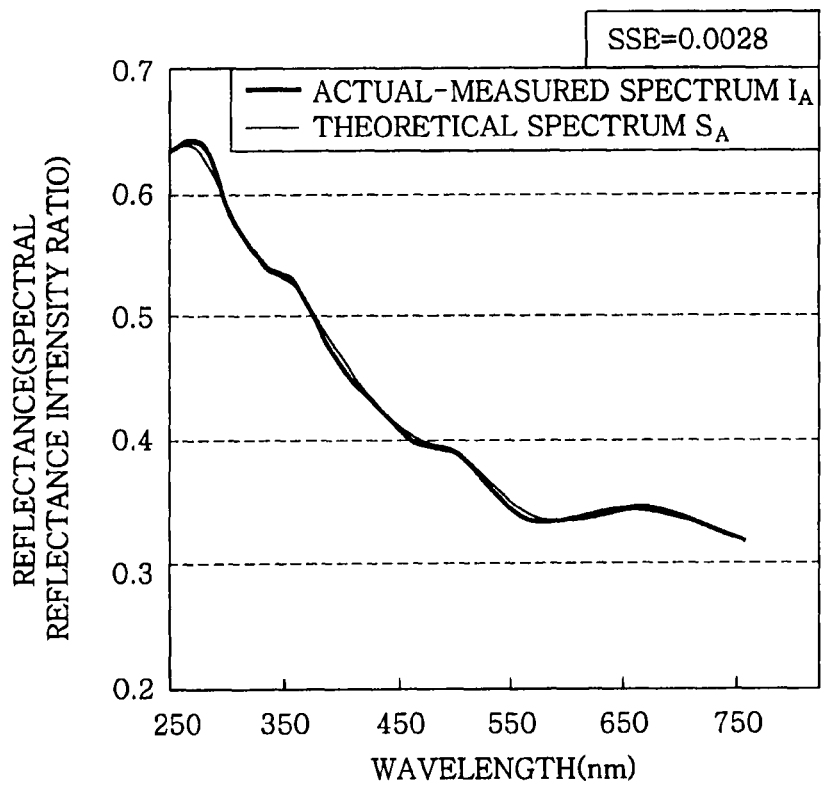
FIG. 14 is a graph showing a theoretical spectrum and an actually measured spectrum of a film structure sample A when the summation of each square sum of the errors in FIG. 13 is minimized.

The solid-line curve in FIG. 13 has clearer minimum value than the dashed-line curve. Since a corresponding minimum value becomes clearer by adding the square sum of errors of each of the fittings, it is possible to acquire an adequate combination of the parameters. In detail, when a value calculated by summing each of the square sums of errors has a minimum value of 0.0042 in the solid-line curve in FIG. 13, the square sum of errors between the theoretical spectrum $S_A$ and the actually measured spectrum $I_A$ is 0.0028 as shown in FIG. 14. The curve of FIG. 14 indicates that the accuracy in the fitting of the spectrums $S_A$ and $I_A$ is very satisfactory.

Figure 15:
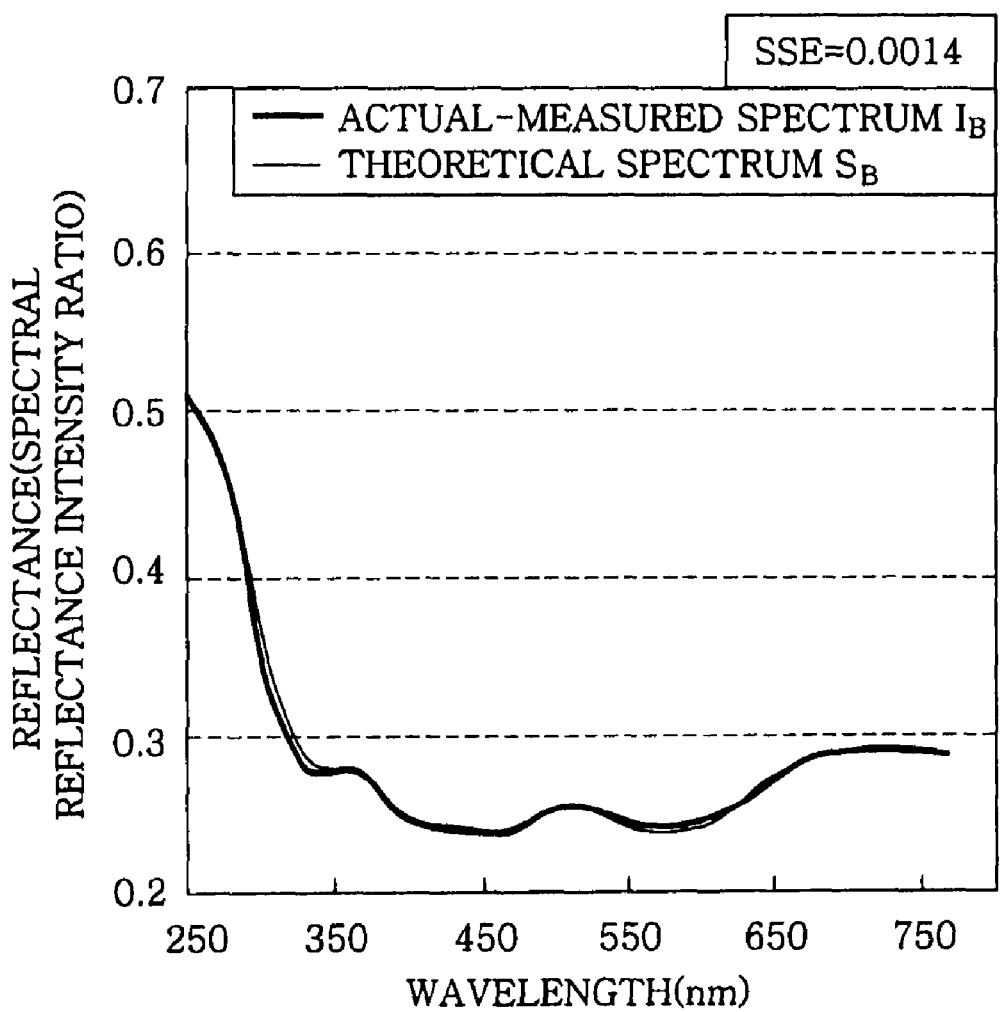
FIG. 15 is a graph showing a theoretical spectrum and an actually measured spectrum of a film structure sample B when the summation of each square sum of the errors in FIG. 13 is minimized.

Moreover, in FIG. 13, the minimum value in the solid-line curve is not identical to that in the dashed-line curve and the minimum value in the dashed-line curve is close to one of local smallest solutions. This may indicate that the optical constants of the polysilicon film 530a are corrected into a physically correct value by simultaneously performing each of the fittings by use of the re-obtaining process in accordance with the present invention. In detail, when the value calculated by summing each of the square sums of errors in the solid-line curve in FIG. 13 has the minimum value of 0.0042, the square sum of errors between the theoretical spectrum $S_B$ and the actually measured spectrum $I_B$ is 0.0014 as shown in FIG. 15. The curves in FIG. 15 indicates that the coincidence of the spectrums $S_B$ and $I_B$ is significantly improved as compared with that of the spectrums $S_B$ and $I_B$ (the square sum of errors therebetween is 0.0664) as shown in FIG. 11 when the only optical constants of the oxide film 540b was obtained. The curve of FIG. 15 indicates that the accuracy in the fitting of the spectrums $S_B$ and $I_B$ is very satisfactory.

As such, in accordance with the re-obtaining process of the present embodiment, since optical constants of a below-located sample film that is located below a target sample film are correctable and optical constants of the target film is re-acquirable, the optical constants of the below-located sample film may be corrected to physically correct values, thereby improving the accuracy in obtaining the optical constants of the target sample film more greatly.

Moreover, the re-obtaining process of the present embodiment is applicable to both the aforementioned case of the oxide film 540b as the target sample film and a case that the fitting is unsatisfactorily performed when optical constants of other target sample films are obtained in the basic process. In this case, when a plurality of sample films, optical constants of which have been already obtained, is located below a target sample film, a re-fitting is simultaneously performed by using an actually measured spectrum of a closest below-located one of the below-located sample films. Nevertheless, if the re-fitting is not satisfactorily performed, the re-fitting is simultaneously performed by using actually measured spectrums of two closest below-located sample films. As such, until the re-fitting is satisfactorily performed, the re-fitting may be simultaneously performed by using actually measured spectrums of below-located sample films while successively increasing the used sample films.

FIG. 16 is a table showing a flow of the basic process and re-obtaining process in accordance with the present embodiment to obtain the optical constants of each film of the film-stacked structure 500 shown in FIG. 5. In a first step of a first stage, optical constants $n_{1a1}$ and $k_{1a1}$ of the polysilicon film 530a as a first target sample film are obtained. Here, as described below, the fitting of the actually measured spectrum $I_A$ and the theoretical spectrum $S_A(P_1$ and $d_{A1})$ for the film structure sample A in FIG. 6 is performed in the basic step of the fitting process shown in FIG. 7. For the obtained optical constants $n_{1a1}$ and $k_{1a1}$ of the first target sample film, the re-obtaining process is not performed. Then, optical constants of a next target sample film are obtained. This is because there is no below-located sample film, optical constants of which have been already obtained to simultaneously perform the fitting in the first step.

Then, in a first step of a second stage, optical constants $n_{2b1}$ and $k_{2b1}$ of the oxide film 540b as a target sample film are obtained. Here, as described below, the fitting of the actually measured spectrum $I_B$ and the theoretical spectrum $S_B(P_2, d_{B1},$ and $d_{B2})$ for the film structure sample B in FIG. 6 is performed in the basic step of the fitting process shown in FIG. 7. As a result, if the fitting is unsatisfactorily performed, a second step of the second stage is started.

As described above, if the fitting is unsatisfactorily performed in the first step of the second stage, optical constants $n_{2b2}$ and $k_{2b2}$ of the oxide film 540b as a target sample film and optical constants $n_{1b2}$ and $k_{1b2}$ of a polysilicon film 530b as a below-located sample film are obtained and modified in the second step of the second stage. Here, as described above, the fitting of the actually measured spectrum $I_B$ and the theoretical spectrum $S_B$ ($P_1, P_2, d_{B1},$ and $d_{B2})$ for the film structure sample B and the fitting of the actually measured spectrum $I_A$ and the theoretical spectrum $S_A(P_1$ and $d_{A1})$ for the film structure sample A are simultaneously performed in the recalculating process as shown in FIG. 12. The fittings are performed by putting a common value for the common optical constant parameter $P_1$ and varying the common optical constant parameter $P_1$.

Then, in a first step of a third stage, optical constants $n_{3c1}$ and $k_{3c1}$ of the BARC film 550c are obtained. Here, as described below, the fitting of the actually measured spectrum $I_C$ and the theoretical spectrum $S_C(P_3, d_{C1}, d_{C2},$ and $d_{C3})$ for the film structure sample C shown in FIG. 6 is performed in the basic step of the fitting process shown in FIG. 7. As a result, if the fitting is unsatisfactorily performed, a second step of the third stage is started.

As described above, if the fitting is unsatisfactorily performed in the first step of the third stage, the optical constants $n_{3c2}$ and $k_{3c2}$ of the BARC film 550c as a target sample film and optical constants $n_{2c2}$ and $k_{2c2}$ of an oxide film 540c as a below-located sample film are re-obtained and modified in the second step of the third stage. Here, as described above, the fitting of the actually measured spectrum $I_C$ and the theoretical spectrum $S_C(P_2, P_3, d_{C1}, d_{C2},$ and $d_{C3})$ for the film structure sample C and the fitting of the actually measured spectrum $I_B$ and the theoretical spectrum $S_B$ ($P_2, d_{B1},$ and $d_{B2})$ for the film structure sample B are simultaneously performed in the re-obtaining process including the fitting operation in FIG. 12. The fittings are performed by putting a common value into the common optical constant parameter $P_2$ and varying the common optical constant parameter $P_1$. Nevertheless, if the fitting is not satisfactorily performed, a third step of the third stage is started.

As described above, if the fitting is not satisfactorily performed in the second step of the third stage, optical constants $n_{1c3}$ and $k_{1c3}$ of a polysilicon film 530c as a further below-located film are also re-obtained and modified in the third step of the third stage. Here, as described above, the fitting of the actually measured spectrum $I_C$ and the theoretical spectrum $S_C(P_1, P_2, P_3, d_{C1}, d_{C2},$ and $d_{C3})$ for the film structure sample C, the fitting of the actually measured spectrum $I_B$ and the theoretical spectrum $S_B(P_1, P_2, d_{B1},$ and $d_{B2})$ for the film structure sample B, and the fitting of the actually measured spectrum $I_A$ and the theoretical spectrum $S_A(P_1$ and $d_{A1})$ for the film structure sample A are simultaneously performed to the obtain the optical constants $n_{1c3}$ and $k_{1c3}$, $n_{2c3}$ and $k_{2c3}$, and $n_{3c3}$ and $k_{3c3}$ in the re-obtaining process including the fitting operation in FIG. 12. The fittings are performed by putting common values for the common optical constant parameters $P_1$ and $P_2$ and varying the common optical constant parameter $P_1$ and $P_2$.

Then, in a first step of a fourth stage, optical constants $n_{4d1}$ and $k_{4d1}$ of the BARC film 560d are obtained. Here, as described below, the fitting of the actually measured spectrum $I_C$ and the theoretical spectrum $S_D(P_4, d_{D1}, d_{D2}, d_{D3}, \text{and } d_{D4})$ for the film structure sample D shown in FIG. 6 is performed in the basic step of the fitting process shown in FIG. 7. As a result, if the fitting is satisfactorily performed, the processing is ended.

If the fitting is not satisfactorily performed in the first step of the fourth stage, and optical constants $n_{4d2}$ and $k_{4d2}$ of a BARC film 560d as a target sample film and optical constants $n_{3d2}$ and $k_{3d2}$ of a BARC film 550d as the below-located film are re-obtained and modified in the second step of the fourth stage. Here, as described above, the fitting of the actually measured spectrum $I_D$ and the theoretical spectrum $S_D(P_3, P_4, d_{D1}, d_{D2}, d_{D3} \text{ and } d_{D4})$ for the film structure sample D and the fitting of the actually measured spectrum $I_C$ and the theoretical spectrum $S_C(P_3, d_{C1}, d_{C2} \text{ and } d_{C3})$ for the film structure sample C are simultaneously performed in the re-obtaining process including the refitting operation in FIG. 12. The fittings are performed by putting a common value for the common optical constant parameter $P_3$ and varying the common optical constant parameter $P_3$. As a result, if the fitting is satisfactorily performed, the processing is ended. If the fitting is unsatisfactorily performed in the second step of the fourth stage, the optical constants $n_{2d3}$ and $k_{2d3}$ of an oxide film 540d as a further below-located film are also re-obtained and modified in the third step of the fourth stage. Here, as described above, the fitting of the actually measured spectrum $I_D$ and the theoretical spectrum $S_D(P_2, P_3, P_4, d_{D1}, d_{D2}, d_{D3}, \text{and } d_{D4})$ for the film structure sample D, the fitting of the actually measured spectrum $I_C$ and the theoretical spectrum $S_C(P_2, P_3, d_{C1}, d_{C2}, \text{and } d_{C3})$ for the film structure sample C, and the fitting of the actually measured spectrum $I_B$ and the theoretical spectrum $S_B(P_2, d_{B1}, \text{and } d_{B2})$ for the film structure sample B are simultaneously performed to obtain optical constants $n_{2d3}$ and $k_{2d3}$, $n_{3d3}$ and $k_{3d3}$, and $n_{4d3}$ and $k_{4d3}$ in the re-obtaining process including the fitting operation shown in FIG. 12. The fittings are performed by putting common values for the common optical constant parameters $P_2$ and $P_3$ and varying the common optical constant parameter $P_2$ and $P_3$. As a result, if the fitting is satisfactorily performed, the processing is ended.

If the fitting is unsatisfactorily performed in the third step of the fourth stage, the optical constants $n_{2d4}$ and $k_{2d4}$ of an oxide film 530d as an even further below-located film are also re-obtained and modified in the fourth step of the fourth stage. Here, as described above, the fitting of the actually measured spectrum $I_D$ and the theoretical spectrum $S_D(P_1, P_2, P_3, P_4, d_{D1}, d_{D2}, d_{D3}, \text{and } d_{D4})$ for the film structure sample D, the fitting of the actually measured spectrum $I_C$ and the theoretical spectrum $S_C(P_1, P_2, P_3, d_{C1}, d_{C2}, \text{and } d_{C3})$ for the film structure sample C, the fitting of the actually measured spectrum $I_B$ and the theoretical spectrum $S_B(P_1, P_2, d_{B1}, \text{and } d_{B2})$ for the film structure sample B, and the fitting of the actually measured spectrum $I_A$ and the theoretical spectrum $S_A(P_1 \text{ and } d_{A1})$ for the film structure sample A are simultaneously performed to obtain optical constants $n_{1d4}$ and $k_{1d4}$, $n_{2d4}$ and $k_{2d4}$, $n_{3d4}$ and $k_{3d4}$, and $n_{4d4}$ and $k_{4d4}$ in the re-obtaining process including the fitting operation shown in FIG. 12. The fittings are performed by putting common values for the common optical constant parameters $P_1$, $P_2$ and $P_3$ and varying the common optical constant parameter $P_1$, $P_2$ and $P_3$. As a result, if the fourth step is completed, the processing is ended.

As such, when a plurality of sample films, optical constants of which have been already obtained, is located below a target sample film, a re-fitting is simultaneously performed by successively reading corresponding actually measured spectrums from a closest below-located one of the below-located films toward the bottom to obtain the optical constants of the target sample film while correcting the optical constants of the below-located sample films. Accordingly, the optical constants of the below-located sample films can be corrected to physically correct values, thereby improving the accuracy in obtaining the optical constants of the below-located sample films. Further, it is possible to greatly improve the accuracy in obtaining the optical constants of the target sample film.

To determine whether the fitting is satisfactorily performed in each step, e.g., curves of the theoretical spectrum S and the actually measured spectrum I may be displayed on a display or the like to enable an operator to check coincidence of the curves or a fitting determining process may be performed to have the control device to automatically determine the coincidence.

In the fitting determining process, it is determined whether, e.g., a square sum of errors of a fitting in the basic process or a value obtained by summing a square sum of errors of each fitting in the re-obtaining process is equal to or smaller than a predetermined threshold value. If the square sum of errors is equal to or smaller than the predetermined value, it is determined that the fitting is satisfactorily performed (determination ok). If the square sum of errors is not equal to or greater than the predetermined threshold value, it is determined that the fitting is unsatisfactorily performed (determination NG). Here, the predetermined threshold value is, e.g., a two decimal digit number ($10^{-2}$ order).

Next, an example of creating an optical model by using the obtained optical constants of each film and examining a surface structure of the wafer W will be described. For example, optical models in which trenches are optically represented by using the obtained optical constants of films are created for trenches of different CD values and are stored in advance in the data storage unit 460. Then, it is possible to examine a CD value of a trench by measuring a surface reflectance of a wafer W as a target object for examining its surface structure and selecting an optical model of the trench corresponding to the surface reflectance. As such, a CD value of a trench can be accurately examined by creating an optical model in which a trench is optically represented by use of accurate optical constants of each film and selecting one of the created optical models.

Figure 17:
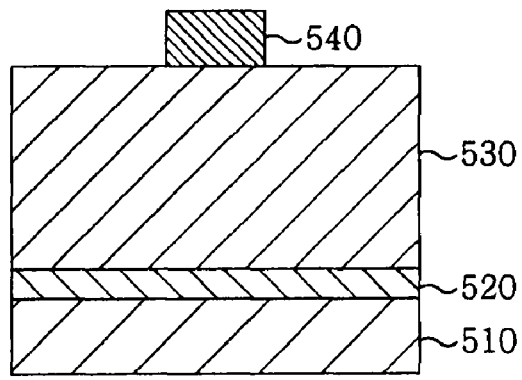
FIG. 17 shows a film structure used to develop an optical model by using optical constants of each film.
Figure 18:
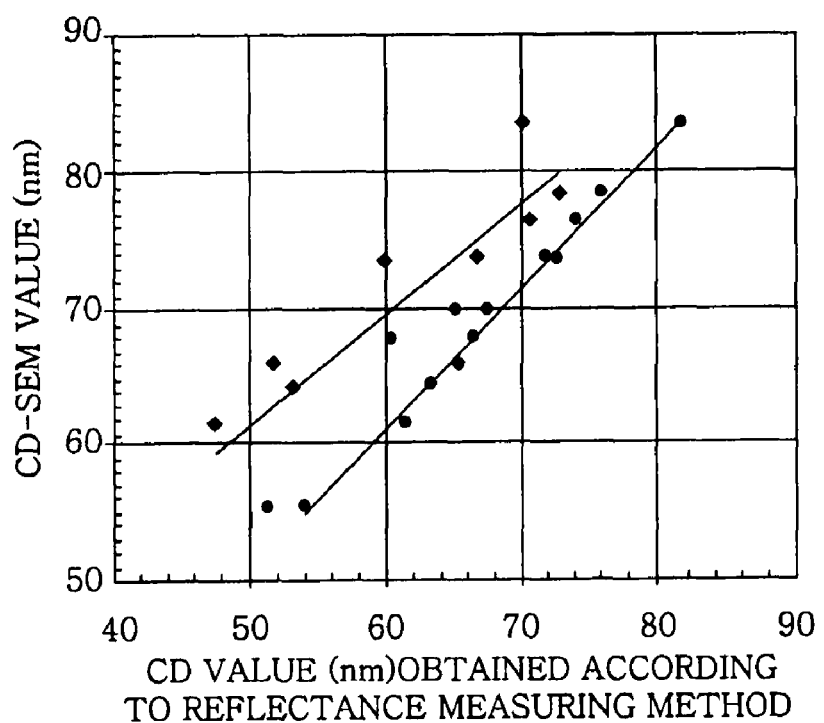
FIG. 18 is a graph showing a correlation between a CD-SEM value and a CD value by a spectral reflectance measuring method.

Below described is an experimental result of comparing a case of creating an optical model by using optical constants of each film obtained based on the basic process with a case of creating an optical model by using optical constants of each film re-obtained based on the re-obtaining process. Here, an optical model is created to examine a CD value of a trench on an oxide 540' in a film structure sample 501 on a wafer W shown in FIG. 17 by using optical constants of each film and a plurality of CD values are examined. For a trench, a CD value of which is measured by such a spectral reflectance measuring method, the CD value (CD-SEM value) is accurately measured by a scanning electron microscope (SEM). FIG. 18 shows a correlation between the CD value and the CD-SEM value by the spectral reflectance measuring method. In FIG. 18, as a gradient of a straight line showing the correlation becomes 1, the correlation becomes greater.

Figure 19:
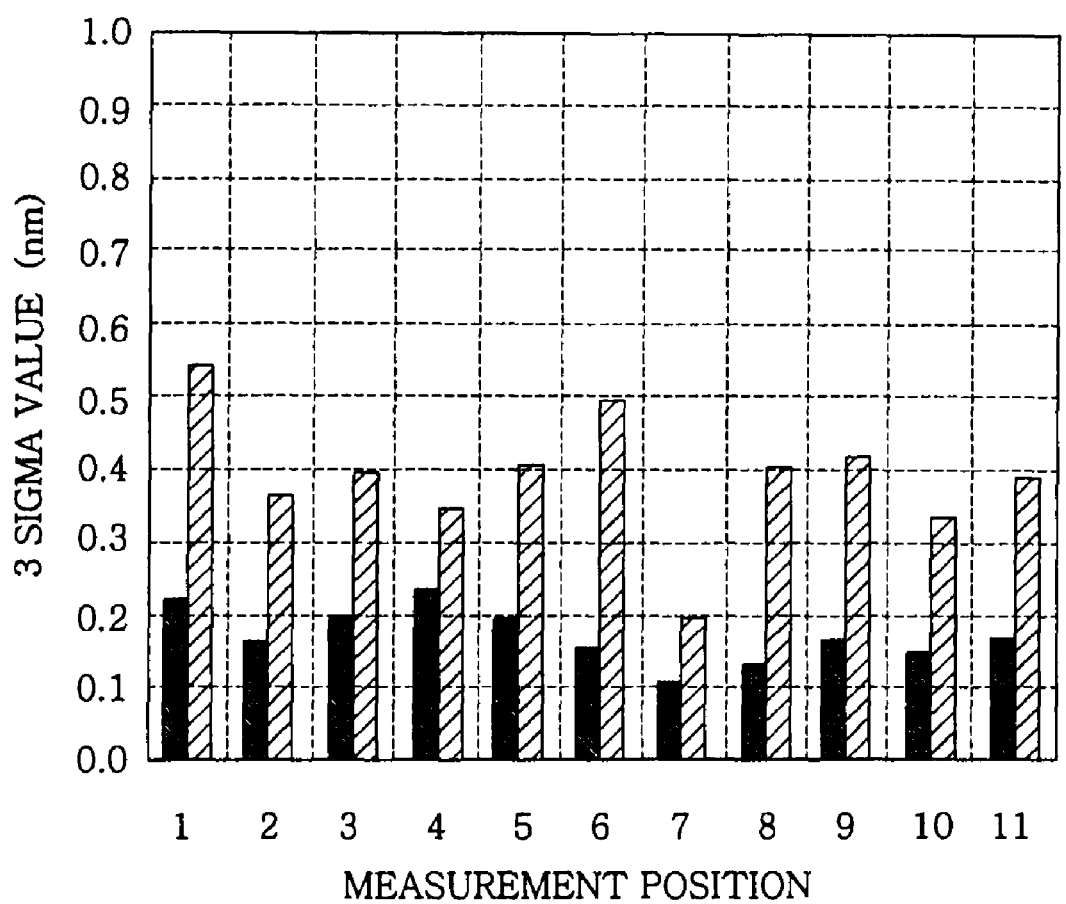
FIG. 19 shows a measurement reproducibility when a CD value is measured at a same position in plural times.

FIG. 19 is a bar graph showing standard errors (3 sigma values) of regression lines when the CD values of 11 positions is respectively measured 30 times. In other words, FIG. 19 shows a measurement reproducibility when the CD value is measured at the same position in plural times. As the 3 sigma values become getting smaller, the measurement reproducibility becomes higher.

For the case of creating the optical model by using the optical constants of each film acquired based only on the basic process to obtain the CD value, [♦] is used in FIG. 18 and the diagonal-line bar graph is used in FIG. 19. For the case of creating the optical model by using the optical constants of each film acquired based on the re-obtaining process to obtain the CD value, [●] is used in FIG. 18 and the shaded bar graph is used in FIG. 19.

Based on FIG. 18, in the case of performing the basic process, the gradient of straight line is 0.81. In contrast, in the case of performing the re-obtaining process, the gradient is 1.05. Accordingly, it is recognized that higher correlation between the CD value and the CD-SEM value and more accurate physical dimension may be obtained by performing the re-obtaining process as compared with performing only the basic process. Based on FIG. 19, in the case of performing the basic process, the bars have ½ 3-sigma values at almost all measuring positions as compared with the case of performing the re-obtaining process. This indicates that higher measurement reproducibility may be obtained by performing the re-obtaining process as compared with performing only the basic process.

Figure 20:
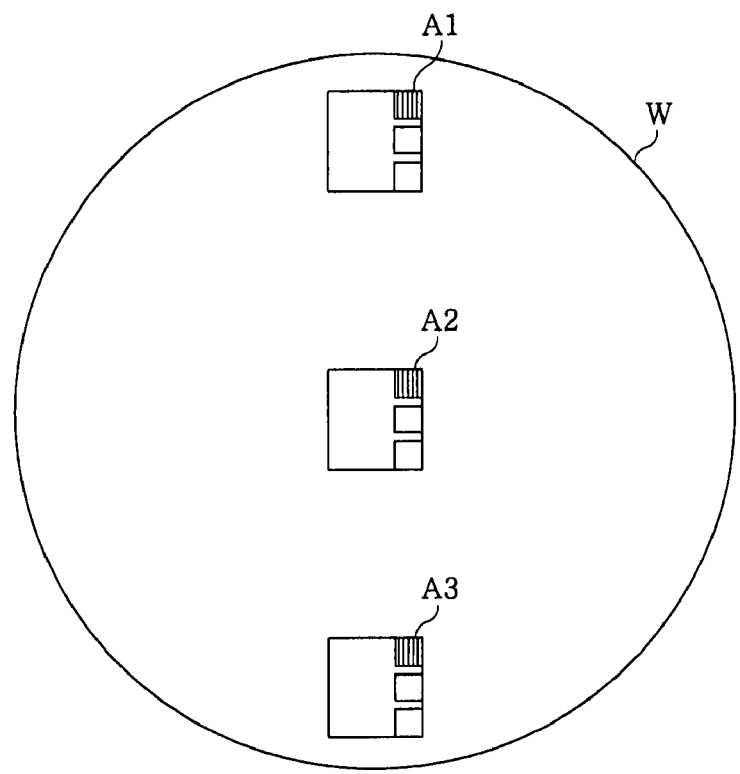
FIG. 20 shows a measurement position on a surface of a wafer.

In the present embodiment, for the used film structure samples A to D, the actually measured spectrums of reflectance are measured from reflection beams of white beams irradiated to any one of the measurement positions A1, A2, and A3 formed on the wafer W, e.g., as shown in FIG. 20. However, the present invention is not limited to this embodiment when the optical constants of each film are obtained. Alternatively, the actually measured spectrums of reflectance may be measured from reflection beams of white beams irradiated to all the measurement positions A1, A2, and A3 to simultaneously perform the fittings of the actually measured spectrums.

In the recalculating process of the present embodiment, the square sum of errors are calculated as the difference between the actually measured spectrums and the respective theoretical spectrums and the fittings are performed to minimize a value calculated by summing each square sum of errors. The present invention, however, is not limited to this embodiment. Alternatively, the square sum of errors may be calculated as the difference between the actually measured spectrums and the respective theoretical spectrums and the fittings may be performed to minimize a value acquired by the multiplication of each square sum of errors. This may bring about the same result as the present embodiment.

In accordance with the present embodiment, the measuring chamber 300 has the structure shown in FIG. 3. That is, the measuring chamber 300 functions as a so-called reflectometer that vertically emits a white beam to a surface of a wafer W and detects a reflection beam of the emitted white beam. The optical constants are obtained based on the reflection beam. The measuring chamber, however, is not limited to this embodiment. For example, a measuring chamber 300' may function as a so-called ellipsometer that obliquely emits a white beam to a surface of a wafer W and detects a reflection beam of the emitted white beam. The optical constants may be obtained based on the reflection beam.

Figure 21:
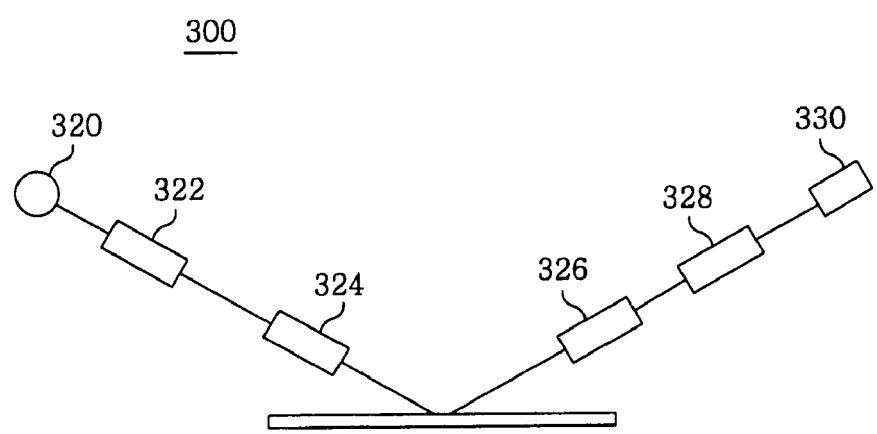
FIG. 21 schematically shows an example of another structure of the measuring chamber shown in FIG. 1.

FIG. 21 shows another example of the measuring chamber, which functions as the ellipsometer. The measuring chamber 300' in FIG. 21 includes a light source (LS) 320, a polarizer 322, a compensation plate (CP) 324, a detector 326, a spectrometer 328, and a detector 330. The light source 320, the polarizer 322, and the compensation plate 324 are arranged along a straight line of a preset angle with respect to a surface of a wafer W. The detector 326, the spectrometer 328, and the detector 330 are arranged symmetrically with the light source 320, the polarizer 322, and the compensation plate 324 with respect to a vertical axis of the wafer W.

In the measuring chamber 300' in FIG. 21, it is possible to measure a reflection beam reflected from the surface of the wafer W. In detail, a white beam irradiated from the light source 320 travels through the polarizer 322 and the compensation plate 324 and incident on the wafer W. The incident white beam is reflected on the surface of the wafer W and a reflection beam of the white beam travels through the detector 326 and the spectrometer 328 and incident on the detector 330. The detector 330 receives the incident reflection beam and converts the received reflection beam to an electric signal to transmit the electric signal to the control device 400.

In the structure of the ellipsometer shown in FIG. 21, a white beam is obliquely irradiated and a reflection beam of the white beam is measured. Accordingly, an optical path through which the white beam travels in a film of a surface of a wafer W is longer than that in the reflectometer that vertically emits a white beam and detects a reflection beam of the white beam. Further, there are more information amount at a position where the beam may be divided, by the polarization, into a longitudinal wave and a transverse wave, spectrums of each reflectance of which are acquirable. Accordingly, the accuracy in the obtaining of the optical constants in the ellipsometer is higher than that in the reflectometer. Moreover, it is possible to more greatly improving the accuracy in the obtaining of the optical constants by applying the basic process and the re-obtaining process in accordance with the present embodiment.

However, in the ellipsometer, since the white beam is obliquely irradiated, a shape of the spotlight beam is an ellipse and becomes longer in a major axis direction. In contrast, in the reflectometer, since the white beam vertically irradiated, a shape of the spotlight beam is a circle. Accordingly, the spotlight beam can be measured at narrower region in the reflectometer than in the ellipsometer. This makes it possible to satisfy the recent trend that requires a spotlight beam having smaller area required for the measurement in accordance with the miniaturization of a design rule of semiconductor devices formed on the wafer W. Though, in general, it is difficult to accurately calculate optical constants in the measurement by reflectometer because of the small amount of information available on a film from a spectrum of reflectance. However, by applying the basic step and the recalculating step for calculating the optical constants in accordance with the present invention to the measurement by the reflectometer, it can become very effective to accurately obtain optical constants of a target film while correcting optical constants of a film that is located below the target film.

In the aforementioned process of examining the surface structure, the case of using the spectral reflectance measuring method as the scatterometry has been described as an example. Alternatively, any method capable of examining a surface structure from a phase and an intensity of a reflection beam of a white beam emitted to a wafer W may be used. For example, an elipsometry may be used.

In the substrate processing apparatus 100 shown in FIG. 1, the measuring chamber 300 is installed in the transfer 130. The present invention is not limited to the embodiment. Alternatively, the measuring chamber 300 may be installed independent of the substrate processing apparatus 100 and at a position different from that of the substrate processing apparatus 100.

The aforementioned embodiment of the present invention may be applied to a system including a plurality of elements or an apparatus of a single element. The purpose of the present invention is achieved by providing a system or an apparatus with a medium such as a storage medium or the like storing program codes of software realizing the functions of the present embodiment and allowing a computer (or a central processing unit (CPU) and/or a microprocessor unit (MPU)) to read and execute the program codes stored in the medium.

In this case, the codes themselves read from the medium realize the functions of the aforementioned embodiment, and thus the present invention includes the medium storing the program codes. The medium for providing the program codes may be, e.g., a floppy (registered trademark) disk, a hard disk, a magneto-optical disk, CD-ROM, CD-R, CD-RW, DVD-ROM, DVD-RAM, DVD-RW, and DVD+RW, a magnetic tape, a nonvolatile memory card, ROM, or the like. The program codes may be provided to a medium by being downloaded through networks.

The functions of the aforementioned embodiment can be realized by executing the program codes read by the computer or by the actual processing partially or wholly executed by an operating system (OS) or the like operated on the computer in accordance with the instructions of the programs.

In addition, the functions may also be realized by the actual processing partially or wholly executed by a CPU or the like in a built-in function extension board or an external function extension unit of a computer in accordance with the instructions of program codes read from a storage medium after the program codes are inputted to a memory in the built-in function extension board or the external function extension unit.

In accordance with the embodiment of the present invention, when optical constants of each film of a film-stacked structure on a substrate are obtained, previously obtained optical constants of a below-located film(s) that is located below a target film may be corrected to physically correct values by correcting both optical constants of the target film located above the below-located film(s) and the previously obtained optical constants of the below-located film(s). Accordingly, it is possible to improve the obtaining accuracy in the optical constants of the target film as well as the below-located film(s).

The aforementioned embodiment of present invention is applicable to a substrate processing apparatus, an optical constant obtaining method, and a storage medium storing a program that executes the optical constant obtaining method. While the invention has been shown and described with respect to the embodiments, it will be understood by those skilled in the art that various changes and modification may be made without departing from the scope of the invention as defined in the following claims.

What is claimed is:

1. A method of obtaining optical constants of films in a film-stacked structure formed on a substrate, the method comprising:
   a basic process obtaining an optical constant of each of the films by successively providing the films one by one as a target film from bottom to top and obtaining an optical constant of the target film by using a previously obtained optical constant of a below-located film that is located directly below the target film; and
   a re-obtaining process for correcting the optical constant of the target film obtained in the basic process by varying the previously obtained optical constant of the below-located film.

2. The method of claim 1, wherein the re-obtaining process comprising:
   acquiring an actually measured spectrum of a spectral reflectance from a reflection beam of a white beam emitted to each of a first and a second film structure sample, wherein the first film structure sample includes a top layer, which serves as a target film of the first film structure sample, and an under-film structure located below the top layer and the structure of the first film structure sample is identical to that of the film-stacked structure; and the second film structure sample includes a top layer, which serves as a target film of the second film structure sample, and the top layer of the second film structure sample and the below-located film located directly below the top layer of the first film structure sample are formed of a same material, and the structure of the second film structure sample is identical to the under-film structure,
   calculating, for each of a plurality combinations of parameter values, a theoretical spectrum of a spectral reflectance from each of the film structure samples;
   performing a fitting operation to the actually measured spectrum and the theoretical spectrum for each of the film structure samples and acquiring a combination of parameter values minimizing a value acquired by summing the difference between the actually measured spectrum and the respective theoretical spectrum for the first film structure sample and that for the second film structure sample; and
   obtaining the optical constants of the target film and the below-located film of the first film structure sample from the acquired combination of parameter values.

3. The method of claim 2, wherein the theoretical spectrum for the first film structure sample is obtained by using parameters including an optical constant and a film thickness of the target film of the first film structure sample and an optical constant and a film thickness of the below-located film of the first film structure sample,
   the theoretical spectrum for the second film structure sample is obtained by using parameters including an optical constant and a film thickness of the target film of the second film structure sample, and
   when performing the fitting operation, the optical constant of the below-located film of the first film structure sample and that of the target film of the second film structure sample are varied together to have common values.

4. The method of claim 3, wherein, in the re-obtaining process, an initial value of each of the parameters is a previously obtained value.

5. The method of claim 2, wherein the difference between the actually measured spectrum and the theoretical spectrum is acquired as a square sum of errors therebetween.

6. The method of claim 2, wherein a film whose optical constant has been already obtained is located directly below the target film of the second film structure sample, an additional re-obtaining process for correcting the optical constant of the target film obtained in the basic process is performed by varying the obtained optical constant of the film.

7. The method of claim 6, wherein, when performing the fitting operation in the re-obtaining process, it is determined whether the value acquired by summing is equal to or smaller than a threshold value, and the additional re-obtaining process is performed when the value acquired by summing is larger than the threshold value.

8. The method of claim 1, wherein the basic process comprising:
- acquiring an actually measured spectrum of a spectral reflectance from a reflection beam of a white beam emitted to a film structure sample, wherein the film structure sample includes a top layer, which serves as a target film of the film structure sample, and the structure of the film structure sample is identical to that of the film-stacked structure;
- calculating a theoretical spectrum of a spectral reflectance from the film structure sample;
- performing a fitting operation to the actually measured spectrum and the theoretical spectrum for the film structure sample and acquiring a combination of parameter values minimizing a difference between the actually measured spectrum and the theoretical spectrum; and
- obtaining the optical constants of the target film of the film structure sample from the acquired combination of parameter values.

9. The method of claim 8, wherein the theoretical spectrum for the film structure sample is obtained by using parameters including an optical constant and a film thickness of the target film of the film structure sample.

10. A substrate processing apparatus of obtaining optical constants of films in a film-stacked structure formed on a substrate, the apparatus comprising:
- a measuring chamber configured to include at least a light source to emit a white beam over the substrate, a spectrometer to disperse a reflection beam of the white beam into its spectrum, and a detector to detect a beam from the spectrometer; and
- a control device, configured to control the measuring chamber, and
- wherein the control device acquires an actually measured spectrum of a spectral reflectance by emitting a white beam to a substrate formed with a film structure sample required for obtaining an optical constant of each film of the film-stacked structure and detecting a reflection beam of the white beam and performs a basic process of obtaining an optical constant of each of the films by successively providing the films one by one as a target film from bottom to top and obtaining an optical constant of the target film by using a previously obtained optical constant of a below-located film that is located directly below the target film, and a re-obtaining process for correcting the optical constant of the target film obtained in the basic process by varying the previously obtained optical constant of the below-located film.

11. A non-transitory computer-readable storage medium storing a computer-readable program for executing a method of obtaining optical constants of film in a film-stacked structure formed on a substrate, the method comprising:
- a basic process obtaining an optical constant of each of the films by successively providing the films one by one as a target film from bottom to top and obtaining an optical constant of the target film by using a previously obtained optical constant of a below-located film that is located directly below the target film; and
- a re-obtaining process for correcting the optical constant of the target film obtained in the basic process by varying the previously obtained optical constant of the below-located film.

12. The non-transitory computer-readable storage medium of claim 9, wherein the basic process comprising:
- acquiring an actually measured spectrum of a spectral reflectance from a reflection beam of a white beam emitted to a film structure sample, wherein the film structure sample includes a top layer, which serves as a target film of the film structure sample, and the structure of the film structure sample is identical to that of the film-stacked structure;
- calculating a theoretical spectrum of a spectral reflectance from the film structure sample;
- performing a fitting operation to the actually measured spectrum and the theoretical spectrum for the film structure sample and acquiring a combination of parameter values minimizing a difference between the actually measured spectrum and the theoretical spectrum; and
- obtaining the optical constants of the target film of the film structure sample from the acquired combination of parameter values.

13. The non-transitory computer-readable storage medium of claim 12, wherein the theoretical spectrum for the film structure sample is obtained by using parameters including an optical constant and a film thickness of the target film of the film structure sample.

* * * * *